United States Patent
Aikawa et al.

(10) Patent No.: US 9,816,090 B2
(45) Date of Patent: Nov. 14, 2017

(54) METHOD FOR INHIBITING CALCIFICATION OF A MACROPHAGE-DERIVED MATRIX VESICLE

(71) Applicant: THE BRIGHAM AND WOMEN'S HOSPITAL, INC., Boston, MA (US)

(72) Inventors: Elena Aikawa, Chestnut Hill, MA (US); Masanori Aikawa, Chestnut Hill, MA (US); Sophie New, Beckenham (GB); Kevin Croce, West Roxbury, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 14/440,173

(22) PCT Filed: Nov. 1, 2013

(86) PCT No.: PCT/US2013/067963
§ 371 (c)(1),
(2) Date: May 1, 2015

(87) PCT Pub. No.: WO2014/071128
PCT Pub. Date: May 8, 2014

(65) Prior Publication Data
US 2015/0315577 A1    Nov. 5, 2015

Related U.S. Application Data

(60) Provisional application No. 61/721,999, filed on Nov. 2, 2012.

(51) Int. Cl.
| | |
|---|---|
| A61K 48/00 | (2006.01) |
| C12N 15/113 | (2010.01) |
| A61K 31/713 | (2006.01) |
| A61K 38/00 | (2006.01) |

(52) U.S. Cl.
CPC .......... *C12N 15/113* (2013.01); *A61K 31/713* (2013.01); *A61K 38/00* (2013.01); *C12N 2310/14* (2013.01); *C12N 2320/30* (2013.01)

(58) Field of Classification Search
CPC .................................................. A61K 48/00
See application file for complete search history.

(56) References Cited

U.S. PATENT DOCUMENTS

| | | | |
|---|---|---|---|
| 2001/0046956 A1 | 11/2001 | Hadcock | |
| 2007/0098812 A1* | 5/2007 | Feinstein | A61K 31/405 424/608 |
| 2011/0166036 A1 | 7/2011 | Nykjaer et al. | |
| 2012/0009174 A1 | 1/2012 | Van Eyk et al. | |
| 2012/0196286 A1 | 8/2012 | Weber et al. | |

FOREIGN PATENT DOCUMENTS

| | | |
|---|---|---|
| JP | 2008239488 A | 9/2008 |
| JP | 2012145570 A | 8/2012 |
| WO | 00/33865 A1 | 6/2000 |
| WO | 2006/047820 A1 | 5/2006 |
| WO | 2011/159762 A1 | 12/2011 |

OTHER PUBLICATIONS

Ma et al. (Journal of Experimental Medicine Nov. 2004, 200 (10) 1337-1346).*
Kapustin et al. "Calcium regulates key components of vascular smooth muscle cell-derived matrix vesicles to enhance mineralization", Circ Res., 109(1):e1-e12 (2011).
New et al., "Cardiovascular Calcification: An Inflammatory Disease", Circulation Journal, 75:1309-1310 (2011).
Al et al., "Activation of ER stress and mTORC1 suppresses hepatic sortilin-1 levels in obese mice", The Journal of Clinical Investigation 122(5):1677-1687 (2012).
Bostrom et al., "The Regulation of Valvular and Vascular Sclerosis by Osteogenic Morphogens", Circulation Research 109(5):564-577 (2011).
Bucay et al., "Osteoprotegerin-deficient mice develop early onset osteoporosis and arterial calcification", Genes & Development 12:1260-1268 (1998).
Campagnolo et al., "Sortilin Expression is Essential for Pro-Nerve Growth Factor-Induced Apoptosis of Rat Vascular Smooth Muscle Cells", PLOS One 9(1):e84969 (2014). (9 pages).
Creemers et al., "Circulating MicroRNAs: Novel Biomarkers and Extracellular Communicators in Cardiovascular Disease?", Circulation Research 110:483-495 (2012).
Desjardins et al., "FGF23 is independently associated with vascular calcification but not bone mineral density in patients at various CKD stages", Osteoporosis International 23:2017-2025 (2012).
Dinsmore et al., "Vascular Calcification in Types II and IV Hyperlipoproteinemia: Radiographic Appearance and Clinical Significance", American Journal of Roentgenology 144:895-899 (1985).
El-Abbadi et al., "Phosphate feeding induces arterial medial calcification in uremic mice: role of serum phosphorus, fibroblast growth factor-23, and osteopontin", Kidney International 75:1297-1307 (2009).
Goettsch et al., "MiR-125b Regulates Calcification of Vascular Smooth Muscle Cells", The American Journal of Pathology 179(4):1594-1600 (2011).
Goettsch et al., "The Osteoclast-Associated Receptor (OSCAR) is a Novel Receptor Regulated by Oxidized Low-Density Lipoprotein in Human Endothelial Cells", Endocrinology 152(12):4915-4926 (2011).
Ichkawa et al., "A Phex Mutation in a Murine Model of X-Linked Hypophosphatemia Alters Phosphate Responsiveness of Bone Cells", Journal of Bone and Mineral Research 27(2):453-460 (2012).

(Continued)

*Primary Examiner* — Kimberly Chong
(74) *Attorney, Agent, or Firm* — Nixon Peabody LLP; David S. Resnick

(57) ABSTRACT

The invention relates to methods for decreasing, inhibiting, preventing, or reducing matrix vesicle induced calcification by inhibiting the amount or formation of a complex comprising phosphatidylserine (PS), annexin II, annexin V or VI, and S100A9 or S100A12 in a macrophage.

12 Claims, 13 Drawing Sheets

(56) References Cited

OTHER PUBLICATIONS

Ishimura et al., "Cross-Sectional Association of Serum Phosphate With Carotid Intima-Medial Thickness in Hemodialysis Patients", American Journal of Kidney Diseases 45(5):859-865 (2005).
Jansen et al., "Roles for the pro-neurotrophin receptor sortilin in neuronal development, aging and brain injury", Nature Neuroscience 10(11):1449-1457 (2007).
Kaddai et al., "Involvement of TNF-α in abnormal adipocyte and muscle sortilin expression in obese mice and humans", Diabetologia 52:932-940 (2009).
Kathiresan et al., "Genome-wide association of early-onset myocardial infarction with common single nucleotide polymorphisms, common copy number variants, and rare copy number variants", Nature Genetics 41(3):334-341 (2009).
Kjolby et al., "Sort1, Encoded by the Cardiovascular Risk Locus 1p13.3, is a Regulator of Hepatic Lipoprotein Export", Cell Metabolism 12:213-223 (2010).
Kwon et al., "Sortilin Associates with Transforming Growth Factor-β Family Proteins to Enhance Lysosome-mediated Degradation", The Journal of Biological Chemistry 286(24):21876-21885 (2011).
Liberman et al., "Oxidant Generation Predominates Around Calcifying Foci and Enhances Progression of Aortic Valve Calcification", Arteriosclerosis, Thrombosis, and Vascular Biology 28:463-470 (2008).
Liu et al., "Pathogenic role of Fgf23 in Hyp mice", American Journal of Physiology, Endocrinology and Metabolism 291:E38-E49 (2006).
Maeda et al., "Sortilin is Upregulated During Osteoblastic Differentiation of Mesenchymal Stem Cells and Promotes Extracellular Matrix Mineralization", Journal of Cellular Physiology 193:73-79 (2002).
Martin et al., "Bone proteins PHEX and DMP1 regulate fibroblastic growth factor Fgf23 expression in osteocytes through a common pathway involving FGF receptor (FGFR) signaling", The FASEB Journal 25:2551-2562 (2011).
Mazella et al., "The 100-kDa Neurotensin Receptor is gp95/Sortilin, a Non-G-Protein-coupled Receptor", The Journal of Biological Chemistry 273(41):26273-26276 (1998).
Munck Petersen et al., "Propeptide cleavage conditions sortilin/neurotensin receptor-3 for ligand binding", The EMBO Journal 18(3):595-604 (1999).
Musunuru et al., "From noncoding variant to phenotype via SORT1 at the 1p13 cholesterol locus", Nature 466 (7307):714-719 (2010).
Nakamura et al., "Coronary Calcification in Patients with Chronic Kidney Disease and Coronary Artery Disease", Clinical Journal of the American Society of Nephrology 4:1892-1900 (2009).
Navarro et al., "Shedding of the luminal domain of the neurotensin receptor-3/sortilin in the HT29 cell line", Biochemical and Biophysical Research Communications 298:760-764 (2002).
Nielsen et al., "Sortilin/Neurotensin Receptor-3 Binds and Mediates Degradation of Lipoprotein Lipase", The Journal of Biological Chemistry 274(13):8832-8836 (1999).
Nilsson et al., "Endocytosis of Apolipoprotein A-V by Members of the Low Density Lipoprotein Receptor and the Vps10p Domain Receptor Families", The Journal of Biological Chemistry 283(38):25920-25927 (2008).
O'Donnell et al., "Genome-wide Association Study for Coronary Artery Calcification with Follow-up in Myocardial Infarction", Circulation 124(25):2855-2864 (2011).
Okayasu et al., "Low-density Lipoprotein Receptor Deficiency Causes Impaired Osteoclastogenesis and Increased Bone Mass in Mice because of Defect in Osteoclastic Cell-Cell Fusion", The Journal of Biological Chemistry 287 (23):19229-19241 (2012).
Samani et al., "Genomewide Association Analysis of Coronary Artery Disease", New England Journal of Medicine 357 (5):443-453 (2007).
Schoppet et al., "Serum Level of the Phosphaturic Factor FGF23 is Associated with Abdominal Aortic Calcification in Men: The STRAMBO Study", Journal of Clinical Endocrinology and Metabolism 97(4):E575-E583 (2012).
Shanahan et al., "Arterial Calcification in Chronic Kidney Disease: Key Roles for Calcium and Phosphate", Circulation Research 109:697-711 (2011).
Sinha et al., "Vascular calcification: mechanisms and management", The British Journal of Cardiology 15(6):316-321 (2008).
Vaegter et al., "Sortilin associates with Trk receptors to enhance anterograde transport and signaling by neurotrophins", Nature Neuroscience 14(1): (2011). (23 pages).
Wang et al., "Role of TGF-β1 in Bone Matrix Production in Vascular Smooth Muscle Cells Induced by a High-Phosphate Environment", Nephron Experimental Nephrology 115(3):e60-e68 (2010).
Willnow et al., "VPS I0P-domain receptors—regulators of neuronal viability and function", Nature Reviews Neuroscience 9:899-909 (2008).
Zimmermann et al., "RNAi-mediated gene silencing in non-human primates", Nature 441:111-114 (2006).
Aikawa et al., "An HMG-CoA Reductase Inhibitor, Cerivastatin, Suppresses Growth of Macrophages Expressing Matrix Metalloproteinases and Tissue Factor In Vivo and In Vitro", Circulation 103:276-283 (2001).
Aikawa et al., "Multimodality Molecular Imaging Identifies Proteolytic and Osteogenic Activities in Early Aortic Valve Disease", Circulation 115:377-386 (2007).
Aikawa et al., "Osteogenesis Associates With Inflammation in Early-Stage Atherosclerosis Evaluated by Molecular Imaging In Vivo", Circulation 116:2841-2850 ( 2007).
Aikawa et al., "Arterial and Aortic Valve Calcification Abolished by Elastolytic Cathepsin S Deficiency in Chronic Renal Disease", Circulation 119:1785-1794 (2009).
Anderson H., "Matrix Vesicles and Calcification", Current Rheumatology Reports 5:222-226 (2003).
Bode et al., "Interaction between S100A8/A9 and Annexin A6 is Involved in the Calcium-induced Cell Surface Exposition of S100A8/A9", The Journal of Biological Chemistry 283(46):31776-31784 (2008).
Chen et al., "Annexin-Mediated Matrix Vesicle Calcification in Vascular Smooth Muscle Cells", Journal of Bone and Mineral Research 23(11):1798-1805 (2008).
Croce et al., "MRP-8/14 is Critical for the Biological Response to Vascular Injury", Circulation 120(5):427-436 (2009).
Goettsch et al., "Sortilin 1 is a novel inducer of vascular calcification", Brigham and Women's Hospital (2012). (2 pages).
Goodman et al., "Vascular Calcification in Chronic Kidney Disease", American Journal of Kidney Disease 43 (3):572-579 (2004).
Grskovic et al., "Depletion of Annexin A5, Annexin A6 and Collagen X Causes No Gross Changes in Matrix Vesicle-Mediated Mineralization, but Lack of Collagen X Affects Hematopoiesis and the Th1/Th2 Response", Journal of Bone and Mineral Research 27(11):2399-2412 (2012).
Kim K., "Calcification of matrix vesicles in human aortic valve and aortic media", Federation Proceedings 35(2):156-162 (1976).
Kirsch et al., Functional Differences Between Growth Plate Apoptotic Bodies and Matrix Vesicles, Journal of Bone and Mineral Research 18(10):1872-1881 (2003).
Li et al., "A dynamic model of calcific nodule destabilization in response to monocyte- and oxidized lipid-induced matrix-metalloproteinases", American Journal of Physiology-Cell Physiology 302:C658-C665 (2012).
Libby et al., "Stabilization of atherosclerotic plaques: New mechanisms and clinical targets", Nature Medicine 8 (11):1257-1262 (2002).
McCormick et al., "S100A8 and S100A9 in Human Arterial Wall. Implications for Atherogenesis", The Journal of Biological Chemistry 280(50):41521-41529 (2005).
New et al., "Abstract 10866: Novel Role of Macrophage-derived Matrix Vesicles in Arterial Microcalcification", Circulation 124:A10866 (2011). (3 pages).
New et al., "Molecular Imaging Insights Into Early Inflammatory Stages of Arterial and Aortic Valve Calcification", Circulation Research 108:1381-1391 (2011).

(56) References Cited

OTHER PUBLICATIONS

Chen et al., "Identification and Characterization of Aortic Valve Mesenchymal Progenitor Cells with Robust Osteogenic Calcification Potential", The American Journal of Pathology 174(3):1109/1119 (2009).

Lefrancois et al., "Inactivation of sortilin (a novel lysosomal sorting receptor) by dominant negative competition and RNA interference", Biological Procedures Online 7(1):17-25 (2005).

Taylor et al., "The cardiac valve interstitial cell", The International Journal of Biochemistry & Cell Biology 35:113-118 (2003).

* cited by examiner

METHOD FOR INHIBITING CALCIFICATION OF A MACROPHAGE-DERIVED MATRIX VESICLE

CROSS REFERENCE TO RELATED APPLICATIONS

This application is a 371 National Phase Entry of International Patent Application No. PCT/US2013/031337 filed on Mar. 14, 2013 which claims the benefit under 35 U.S.C. §119(e) of U.S. Provisional Application No. 61/721,999 filed Nov. 2, 2012, the contents of which are incorporated herein by reference in their entirety.

TECHNICAL FIELD

The present disclosure relates generally to methods and compositions for decreasing, inhibiting, treating, or preventing cardiovascular calcification, e.g., arterial and valvular microcalcification.

BACKGROUND

Cardiovascular calcification is a disease of dysregulated mineral metabolism, which leads to increased risk of cardiovascular events and potentially death. Microcalcifications located in the thin fibrous cap overlying the necrotic core of atherosclerotic plaques may cause microfractures, which can lead to acute thrombosis and even sudden death due to fatal myocardial infarction (Huang H, Circulation, 2001; Virmani R, 2006; Vengrenyuk Y, 2006). Various therapeutic agents have been investigated to target cardiovascular calcification; these include statins (Aikawa E, Circulation, 2007; Monzack et al, 2009; Osman L, Circulation, 2006; Rajamannan N M, Circulation, 2005) and mineralocorticoid receptor antagonists (Gkizas S, Cardiovasc Pharma, 2010; Jaffe I Z, ATVB, 2007), however as yet they have not proved beneficial in the clinical setting (Gilmanov D, Inter. Cardiovasc Thor Surg. 2010). Calcification in the aortic valve causes aortic stenosis and heart failure. However, the only option to treat aortic valve calcification or stenosis is surgical valve replacement, for which many patients with advanced calcification and/or impaired cardiac function have no indication.

Physiological mineralization is initiated in bone and cartilage in association with matrix vesicles released by osteoblasts and chondrocytes (Anderson H C 2003). Due to this it is suggested that they also play a sizeable role in pathological ectopic calcification (Shao J S, Cai J and Towler D A 2006). In medial calcification in patients with chronic kidney disease, vascular smooth muscle cells have already been identified to release calcifying matrix vesicles (30-300 nm) that serve as a nidus for mineral nucleation (Kapustin et al 2011; Reynolds et al 2009). Whilst this is a feasible notion for medial calcification, in intimal calcification where macrophages are in abundance and smooth muscle cells are lacking, macrophages may play a greater role in the calcification process.

Arterial microcalcifications in the thin cap overlying the necrotic core in the intima of atherosclerotic plaques may cause compliance mismatch, increase local stress, and promote microfractures—leading to plaque rupture causing acute cardiovascular events (Libby P. & Aikawa M., Nat Med, 2002, 8:1257-62 and Li et al., Am J Physiol Cell Physiol., 2012, 302:C658-C665). Atherosclerotic plaques containing "spotty" calcifications consisting of calcified vesicles (precursors to microcalcification) have increased stress, thus making them more susceptible to rupture (Wenk et al., J Biomech Eng., 2010, 132:091011).

Patients with chronic renal disease (CRD) have heightened susceptibility to atherosclerosis, a greater risk of intimal and medial calcification, as well as aortic valve stenosis, and a high cardiovascular mortality (Aikawa et al., Circulation, 2009, 119:1785-94 and Goodman et al., Am J Kidney Dis., 2004, 43:572-9). The added complication of hyperphosphatemia, may trigger release of matrix vesicles (MV) also termed as extracellular vesicles (Chen et al., J Bone Miner Res., 2008, 23:1798-805 and Kapustin et al., Circ Res., 2011, 109:e1-12). Cells release MV to initiate mineralization in both non-pathological (Anderson H. C., Curr Rheumatol Rep., 2003, 5:222-6) and pathological conditions (Chen et al., J Bone Miner Res., 2008, 23:1798-805; Kapustin et al., Circ Res., 2011, 109:e1-12; Anderson H. C., Curr Rheumatol Rep., 2003, 5:222-6; and Kim K. M., Fed Proc., 1976, 35:156-62)

Smooth muscle cell (SMC)-derived MV contribute to medial calcification in CRD patients (Kapustin et al., Circ Res., 2011, 109:e1-12) and interstitial valvular cell-derived MV may contribute to aortic valve calcification. Inventors' previous molecular imaging studies co-localized early stages of atherosclerotic intimal calcification/microcalcification with macrophages (Aikawa et al., Circulation, 2007, 116:2841-50). While arterial and valvular calcification promotes heart attacks and aortic valve stenosis, which represent major health problems and economic burden in the United States, no medical therapies are available for calcification.

Therefore, there exists a need for an effective method of inhibiting and preventing cardiovascular calcification, such as arterial and valvular microcalcification.

SUMMARY

In part, this invention is based on inventors' discovery that macrophages play a direct role in arterial and aortic valve calcification by releasing calcifying matrix vesicles (MV), precursors of microcalcifications, which can contribute to accelerated microcalcification formation in CRD (New S. E & Aikawa E., Circ Res., 2011, 108:1381-91). The inventors have discovered that these calcifying matrix vesicles bud from the membrane of the living cells, aggregate and form large calcification regions. This novel mechanism is as an alternative pathway to the commonly accepted mechanisms of SMC osteogenic transition or apoptotic cell death. Once stimulated by pro-inflammatory or pro-atherogenic cues, a complex can form in the membrane, which enables the matrix vesicles to increase in calcium content and thus calcify. The inventors have further discovered that this complex is formed of phosphatidylserine, members of the annexin family (e.g., annexin II/V/VI and S100A9/S100A12. In addition, the inventors have shown in this study that inhibiting the activity of S100A9 in vitro and genetic deficiency in S100A9$^{-/-}$ mice reduced MV calcification, while stimulation with S100A9 increased MV calcification potential.

Accordingly, in one aspect provided herein is a method for decreasing, inhibiting, preventing, or reducing matrix vesicle calcification or matrix vesicle induced calcification. The method comprising contacting a compound with a macrophage, wherein the compound decreases, inhibits, prevents, or reduces: (i) release of the matrix vesicle from the macrophage; (ii) amount or formation of a complex comprising phosphatidylserine (PS), annexin II, V or VI, and S100A9 or S100A12 in the matrix vesicle or the macrophage; or (iii) expression level of a nucleic acid encoding annexin II, annexin V, annexin VI, S100A9, or S100A12 in the macrophage.

In some embodiments, the complex comprises PS, annexin V, and S100A9.

The methods described herein can be used for inhibiting vascular calcification in a subject by administering to the subject a compound, wherein the compound decreases, inhibits, prevents, or reduces: (i) release of the matrix vesicle from the macrophage; (ii) amount or formation of a complex comprising phosphatidylserine (PS), annexin V or VI, and S100A9 or S100A12 in the matrix vesicle or the macrophage; or (iii) expression level of a nucleic acid encoding annexin V, annexin VI, S100A9, or S100A12 in the macrophage.

In some embodiments, cardiovascular calcification is valvular or arterial microcalcification.

In some embodiments, the subject has severe mineral imbalance and calcium/phosphate disorders, including chronic renal disease, hemodyalysis and type II diabetes suffer from accelerated vascular and valvular calcification. For instance, arterio-venous shunts/grafts for hemodialysis in patients with chronic renal disease, vein grafts for peripheral arterial disease in diabetic patients, and saphenous vein bypass grafts for occluded coronary arteries in patients with metabolic disorders are often occluded within a year (vein graft failure). In the future, tissue engineered vascular and valvular implants in patients at metabolic risk may often fail. In addition, patients with Paget's disease, diabetes, rheumatoid arthritis, osteoporosis or osteoarthritis.

In some embodiments, the subject has a transcatheter valve implant. In some embodiments, the subject has chronic coronary atherosclerosis or aortic stenosis.

In some embodiments, vascular calcification is valvular or arterial microcalcification.

BRIEF DESCRIPTION OF THE DRAWINGS

FIG. 1A, calcified vesicular structures (hematoxylin; blue) adjacent to macrophages (CD68; red) in human plaques (n=136). FIG. 1B, Few or no alph smooth muscle actin ($\alpha$SMA)-positive SMC were noted in the same area. FIG. 1C, Ex vivo hydroxyapatite (HA)-binding near-infrared fluorescence (NIRF) imaging agent detected vesicular microcalcification (red) within human and, FIG. 1D, apoE$^{-/-}$ mouse plaques. FIG. 1E-F, Ultrastructure of human calcified plaques: FIG. 1E, CD68-positive cells release CD68-positive MV (immunogold). FIG. 1F, Vesicles of different sizes and appearance. FIGS. 1G and 1H, Ultrastructure of calcified CRD apoE$^{-/-}$ mouse plaque in: FIG. 1G, MV near cholesterol crystals (ChC; AB apoptotic bodies). FIG. 1H, MV (30-300 nm) hydroxyapatite crystallization.

FIG. 2A, still from time-lapse imaging of mouse MV release from RAW264.7, FIGS. 2B and 2C, The intensity of Fluo-3, a calcium (Ca) indicator, within human macrophages (hMac) increased with Ca/P-stimulation, demonstrating calcium influx upon Ca/P-stimulation. The arrow represents the x-axis on the graph. FIGS. 2D and 2E, Various stimuli induce release of MV with increased calcium content from mouse and human macrophages (n= 3-9, *p<0.05, p<0.001, *p<0.0001). FIGS. 2F and 2G, macrophage-derived (Mac-MV) from Ca/P-stimulated mouse macrophages were larger in size and potentially aggregated over time (n=3). FIG. 2H, Ultrastructure of mouse Mac-MV released in vitro, showed membrane-bound MV from control cells (top) and calcifying MV (bottom). FIG. 2I, MV expressed exosomal markers (TSG101 and CD9). FIG. 2J, Ca/P-stimulated mouse macrophages expressed pro-inflammatory markers (M1 phenotype) (n=3, *p<0.01 vs. control). Ca/P=3 mmol/L calcium/2 mmol/L phosphate (P).

FIG. 3A, Expression of S100A9 and Anx5 in calcified CRD apoE$^{-/-}$ mouse plaques (arrows). FIG. 3B, S100A9 and FIG. 3C, Anx5 co-localized with MV in calcified human plaques (immunogold) (arrows point to MV). FIG. 3D, Enriched S100A9 and Anx5 expression in calcifying mouse Mac-MV (n=3). FIG. 3E, S100A9 (green) and annexin V (red) co-localized (yellow) in mouse macrophages; interaction confirmed by co-immunoprecipitation (FIG. 3F, n=3). FIG. 3G, PS externalization noted with Ca/P-stimulation.

FIG. 4A, Addition of S100A9 enhanced the calcific potential of mouse Mac-MV released by murine macrophages (n=8). FIG. 4B, S100A9 small interfering RNA (siRNA) transfection of human macrophages tended to decrease the calcific potential of MV (n=4; *p<0.05). FIG. 4C, MV increased in apoE$^{-/-}$ mouse plasma (n=5) compared to WT (n=8). ApoE$^{-/-}$S100A9$^{-/-}$ mice (n=5) had a lower MV concentration compared to apoE$^{-/-}$. FIG. 4D, Peritoneal macrophages from S100A9$^{-/-}$ mice (n=6) released MV with a lower calcific potential, compared to WT mice (n=7; *p<0.05). FIG. 4E, Proposed mechanism: Stimulated macrophages release MV with a PS-Anx5-S100A9 membrane complex that facilitates the nucleation of hydroxyapatite and generation of microcalcification.

DETAILED DESCRIPTION

Figure 1:
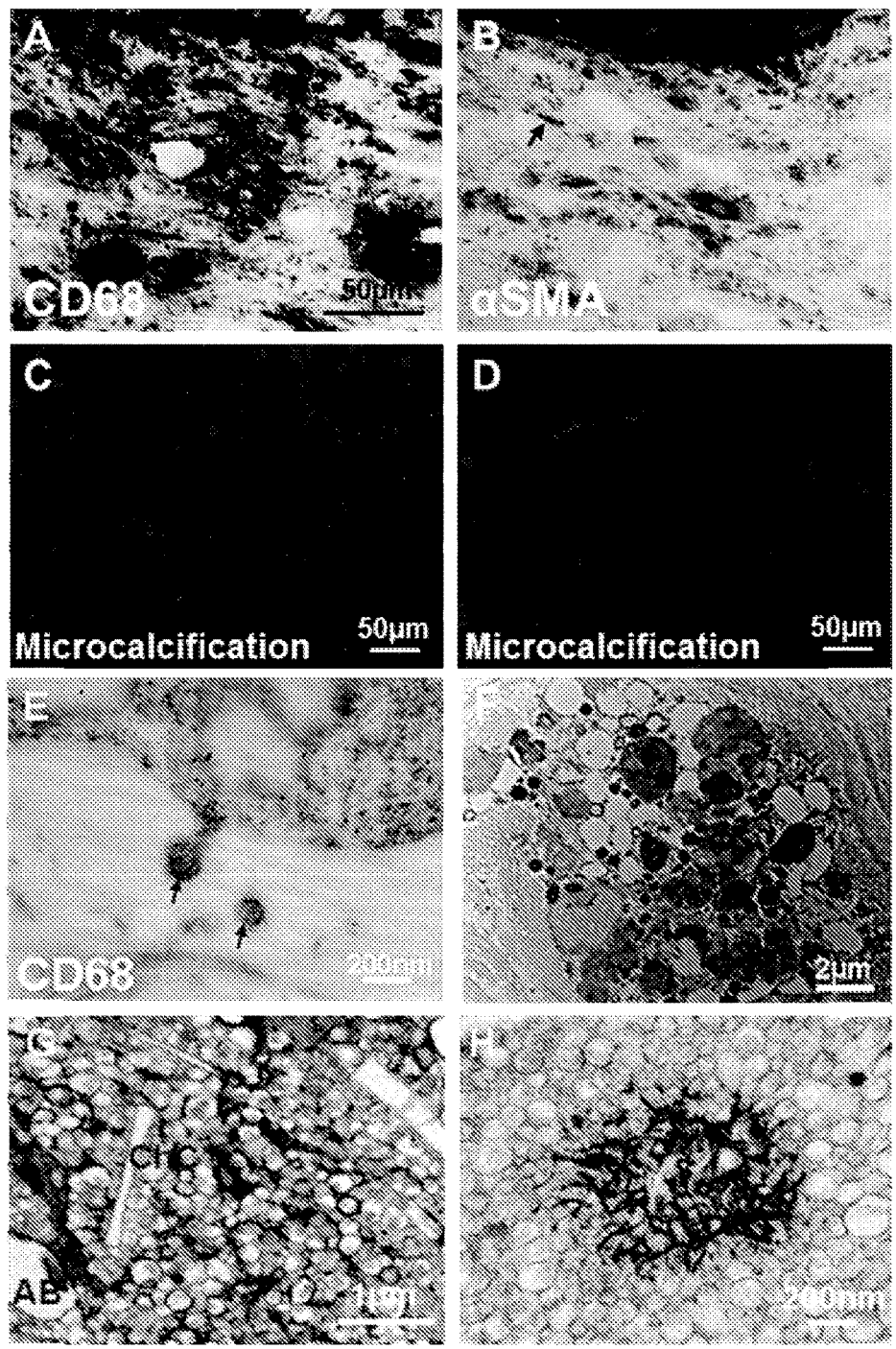
FIGS. 1A-1H show that macrophage-derived MV contribute to atherosclerotic microcalcification.

Based on inventors' previous work, the inventors have now discovered that macrophages play a direct role in arterial microcalcification. Thus, in part, this invention is based on inventors' discovery of an alternative inflammation-related non-osteogenic pathway of arterial calcification in which macrophages release microcalcification-generating matrix vesicles (MV). Specifically, the inventors have discovered that macrophages release calcifying MV, phosphatidylserine, annexin V/VI (Anx5/Anx6) and S100A9, which contribute to accelerated microcalcification formation in CRD. In this study, the inventors have also shown that inhibiting or reducing the amount or the activity of S100A9 in vitro and genetic deficiency in SA100A9−/− mice reduced MV calcification, while stimulation with S100A9 increased calcification potential.

Accordingly, in one aspect, provided herein is a method for decreasing, inhibiting, preventing, or reducing matrix vesicle calcification. Generally the method comprises inhibiting the formation of a complex comprising PS, annexin II/V/VI, and S100A9/A10012. In some embodiments, the method comprising contacting a compound with a macrophage, wherein the compound decreases, inhibits, prevents, or reduces:

(i) release of the matrix vesicle from the macrophage;
(ii) release of the matrix vesicle from the SMC;
(iii) release of the matrix vesicle from the interstitial valvular cell;
(iv) amount or formation of a complex comprising phosphatidylserine (PS), annexin II, V or VI, and S100A9 or S100A12 in the matrix vesicle or the macrophage; or
(v) expression level of a nucleic acid encoding annexin II, annexin V, annexin VI, S100A9, or S100A12 in the macrophage, SMC or interstitial valvular cell.

The compounds which can decrease, inhibit, prevent, or reduce the complex formation are also referred to as complex inhibitors herein. Without limitations, the complex inhibitors include those compounds which can decrease, inhibit, prevent, or reduce:

(i) release of the matrix vesicle from the macrophage;
(ii) release of the matrix vesicle from the SMC;
(iii) release of the matrix vesicle from the interstitial valvular cell;
(iv) amount or formation of a complex comprising phosphatidylserine (PS), annexin II, V or VI, and S100A9 or S100A12 in the matrix vesicle or the macrophage; or
(v) expression level of a nucleic acid encoding annexin II, annexin V, annexin VI, S100A9, or S100A12 in the macrophage, SMC or interstitial valvular cell.

The terms "decrease," "inhibit," "reduced," or "reduction," in reference to: (i) release of the matrix vesicle from the macrophage; (ii) amount or formation of a complex comprising phosphatidylserine (PS), annexin II, V or VI, and S100A9 or S100A12 in the matrix vesicle or the macrophage; or (iii) expression level of a nucleic acid encoding annexin II, annexin V, annexin VI, S100A9, or S100A12 in the macrophage the amount or formation of the complex, generally mean a decrease by a statistically significant amount. However, for avoidance of doubt, "reduced", "reduction" or "decrease" or "inhibit" means a decrease by at least 10% as compared to a reference level, for example a decrease by at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95% but not 100% (e.g. absent level as compared to a reference sample) decrease. In some embodiments, decrease can be 100% (e.g., a level below limit of detection). Reference level can be the level in absence of the inhibitor.

Methods disclosed herein can be used to prevent or treat atherosclerotic calcification, medial calcification, aortic valve calcification, and other conditions characterized by cardiovascular calcification. For example, the methods disclosed herein can be used to prevent or treat cardiovascular calcification in patients with mineral imbalance and calcium/phosphate disorders, including chronic renal disease, chronic renal failure on hemodialysis, diabetes, arteriovenous grafts/shunts, vascular grafts including vein graft for peripheral arterial disease and coronary artery disease, tissue engineered vascular and valvular implants, Paget's disease, rheumatoid arthritis, osteoporosis or osteoarthritis. Without wishing to be bound by a theory, in these indications, progression of cardiovascular calcification can develop within weeks-months. In some embodiments, cardiovascular calcification can be associated with chronic renal insufficiency or end-stage renal disease. In some embodiments, cardiovascular calcification can be associated with pre- or post-dialysis or uremia. In some embodiments, vascular calcification can be associated with diabetes mellitus I or II. In some embodiments, cardiovascular calcification can be associated with a cardiovascular disorder. Without wishing to be bound by a theory, the renal failure can be due to several diseases including diabetes and is often accompanied with hemodialysis, mineral imbalance and calcium/phosphate disorders.

Accordingly, presented herein are also methods for decreasing, inhibiting, preventing, or treating calcification, e.g., vascular calcification, in a subject. The method comprising inhibiting the amount of a complex comprising PS, annexin II/V/VI, and S100A9/S100A12_ in the subject. In some embodiments, the method comprising administering to a subject in need thereof a compound, wherein the compound decreases, inhibits, prevents, or reduces:

(i) release of the matrix vesicle from the macrophage;
(ii) release of the matrix vesicle from the SMC;
(iii) release of the matrix vesicle from the interstitial valvular cell;

(iv) amount or formation of a complex comprising phosphatidylserine (PS), annexin II, V or VI, and S100A9 or S100A12 in the matrix vesicle or the macrophage; or (v) expression level of a nucleic acid encoding annexin II, annexin V, annexin VI, S100A9, or S100A12 in the macrophage, SMC or interstitial valvular cell.

In some embodiments, the complex inhibitor retards or reverses the formation, growth or deposition of extracellular matrix hydroxyapatite crystal deposits. In another aspect, the inhibitor prevents the formation, growth or deposition of extracellular matrix hydroxyapatite crystal deposits.

In some embodiments, the inhibitor can decrease, inhibit, or reduce the release of the complex from a cell, e.g., a macrophage.

In some embodiments, the inhibitor decreases, inhibits or reduces complexation or binding of S100A9 with annexin II, V, annexin VI, and/or PS. In some embodiments, the inhibitor decreases, inhibits or reduces complexation or binding of S100A12 with annexin V, annexin VI, and/or PS.

In some embodiments, the inhibitor decreases, inhibits or reduces complexation or binding of annexin V with S100A9, S100A12, and/or PS. In some embodiments, the inhibitor decreases, inhibits or reduces complexation or binding of annexin VI with S100A9, S100A12 and/or PS. In some embodiments, the inhibitor decreases, inhibits or reduces complexation or binding of PS with annexin V, annexin VI, S100A9 and/or S100A12.

In some embodiments, the inhibitor can decrease or reduce the amount of a component of the complex in the MV or the cell, e.g., amount of PS, annexin V, annexin VI, S100A9 and/or S100A12.

The terms "decrease," "inhibit," "reduced," or "reduction," in reference to complexation or binding between two or more components generally mean a decrease by a statistically significant amount. However, for avoidance of doubt, "reduced", "reduction" or "decrease" or "inhibit" means a decrease by at least 10% as compared to a reference level, for example a decrease by at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95% but not 100% (e.g. absent level as compared to a reference sample) decrease. In some embodiments, decrease can be 100% (e.g., a level below limit of detection). Reference level can be the level in absence of the inhibitor.

Without wishing to be bound by a theory, an inhibitor can act be binding to a site on one of the complex components which site is required for complexation or binding with a second component. Alternatively, the inhibitor can bind to a site on a complex component that is not required for complexation or binding; however binding of the inhibitor blocks or inhibits the complexation. In some cases, the inhibitor can destabilize the formed complex.

In some embodiments, the inhibitor can decrease or reduce the amount of a component of the complex. This can be accomplished by increasing or enhancing the degradation of the component; decreasing or inhibiting the stability of the component; and/or decreasing, reducing or inhibiting the expression of a nucleic acid encoding the component.

Without limitations, the inhibitor, can be selected from the group consisting of small organic or inorganic molecules; saccharines; oligosaccharides; polysaccharides; biological macromolecules, e.g., peptides, proteins, and peptide analogs and derivatives; peptidomimetics; glycoproteins, glycopeptides, antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof.

In some embodiments, the inhibitor is a small molecule. As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

In some embodiments, the inhibitor is a nucleic acid molecule or an analog or derivate thereof. As used herein, the term "nucleic acid" or "oligonucleotide" or grammatical equivalents herein means at least two nucleotides, including analogs or derivatives thereof, that are covalently linked together. Exemplary oligonucleotides include, but are not limited to, single-stranded and double-stranded siRNAs and other RNA interference reagents (RNAi agents or iRNA agents), shRNA (short hairpin RNAs), antisense oligonucleotides, aptamers, ribozymes, and microRNAs (miRNAs). The nucleic acids can be single stranded or double stranded. The nucleic acid can be DNA, RNA or a hybrid, where the nucleic acid contains any combination of deoxyribo- and ribo-nucleotides, and any combination of uracil, adenine, thymine, cytosine and guanine. The nucleic acids can comprise one or more backbone modifications, e.g., phosphoramidate (Beaucage et al., Tetrahedron 49(10):1925 (1993) and references therein; Letsinger, J. Org. Chem. 35:3800 (1970)), phosphorothioate, phosphorodithioate, O-methylphophoroamidite linkages (see Eckstein, Oligonucleotides and Analogues: A Practical Approach, Oxford University Press), or peptide nucleic acid linkages (see Egholm, J. Am. Chem. Soc. 114:1895 (1992); Meier et al., Chem. Int. Ed. Engl. 31:1008 (1992); and Nielsen, Nature, 365:566 (1993), content of all of which is herein incorporated by reference. The nucleic acids can also include modifications to nucleobase and/or sugar moieties of nucleotides. Exemplary sugar modifications at the sugar moiety include replacement of 2'-OH with halogens (e.g., fluoro), O-methyl, O-methoxyethyl, $NH_2$, SH and S-methyl. In some embodiments, the nucleic acid is a peptide nucleic acid (PNA). Without wishing to be bound by a theory, nucleic acid inhibitors can decrease, inhibit, or reduce the expression or amount of the nucleic acid encoding a component of the complex. Computational and experimental methods, including high throughput screening assays, for producing nucleic acid inhibitors, e.g., antisense oligonucleotides, siRNAs, ribozymes, aptamers, and the like, targeted to any target sequence are known in the art and available to one of skill in the art.

In some embodiments, the inhibitor is short interfering RNA (siRNA). The term "short interfering RNA" (siRNA), also referred to herein as "small interfering RNA" is defined as an agent which functions to inhibit expression of a target gene, e.g., by RNAi. A siRNA can be chemically synthesized, it can be produced by in vitro transcription, or it can be produced within a host cell. siRNA molecules can also be generated by cleavage of double stranded RNA, where one strand is identical to the message to be inactivated. The term "siRNA" refers to small inhibitory RNA duplexes that induce the RNA interference (RNAi) pathway. These molecules can vary in length (generally 18-30 base pairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region.

In some embodiments, the inhibitor is an antisense oligonucleotide or siRNA molecule comprising a part of (e.g., 10-50, 12-40, 15-30, 16-25, or 18-22 consecutive nucleotides) of the antisense sequence of a nucleic acid encoding a component of the complex. in length).

In some embodiments, the nucleic acid encoding a component of the complex is an mRNA.

In one embodiment, the inhibitor comprises the nucleic acid sequence GGUCAUAGAACACAUCAUG (SEQ ID NO: 1), GCAGCUGGAACGCAACAUA (SEQ ID NO: 2), CCAAUACUCUGUGAAGCUG (SEQ ID NO: 3), or ACACAAAUCCAGACAAGCA (SEQ ID NO: 4).

In some embodiments, the inhibitor is an antibody or fragment thereof. The terms "antibody" and "antibodies" include polyclonal antibodies, monoclonal antibodies, humanized or chimeric antibodies, single chain Fv antibody fragments, Fab fragments, and F(ab)$_2$ fragments. Antibodies having specific binding affinity for a component of the complex, e.g., PS, annexin V, annexin VI, S100A9, or S100A12, can be produced through standard methods. Alternatively, antibodies may be commercially available, for example, from R&D Systems, Inc., Minneapolis, Minn.

As used herein, the terms "antibody" and "antibodies" refer to intact antibody, or a binding fragment thereof that competes with the intact antibody for specific binding and includes chimeric, humanized, fully human, and bispecific antibodies. In some embodiments, binding fragments are produced by recombinant DNA techniques. In additional embodiments, binding fragments are produced by enzymatic or chemical cleavage of intact antibodies. Binding fragments include, but are not limited to, Fab, Fab', F(ab')$_2$, Fv, and single-chain antibodies. Unless it is specifically noted, as used herein a "fragment thereof" in reference to an antibody refers to an immunospecific fragment, i.e., an antigen-specific or binding fragment.

Monoclonal antibodies, which are homogeneous populations of antibodies to a particular epitope contained within an antigen, can be prepared using standard hybridoma technology. In particular, monoclonal antibodies can be obtained by any technique that provides for the production of antibody molecules by continuous cell lines in culture such as described by Kohler, G. et al., Nature, 1975, 256:495, the human B-cell hybridoma technique (Kosbor et al., Immunology Today, 1983, 4:72; Cole et al., Proc. Natl. Acad. Sci. USA, 1983, 80:2026), and the EBV-hybridoma technique (Cole et al., Monoclonal Antibodies and Cancer Therapy, Alan R. Liss, Inc., 1983, pp. 77-96). Such antibodies can be of any immunoglobulin class including IgG, IgM, IgE, IgA, IgD, and any subclass thereof. The hybridoma producing the monoclonal antibodies of the invention can be cultivated in vitro or in vivo.

Polyclonal antibodies are heterogeneous populations of antibody molecules that are specific for a particular antigen, which are contained in the sera of the immunized animals. Polyclonal antibodies are produced using well-known methods. A chimeric antibody is a molecule in which different portions are derived from different animal species, such as those having a variable region derived from a murine monoclonal antibody and a human immunoglobulin constant region. Chimeric antibodies can be produced through standard techniques. Antibody fragments that have specific binding affinity for a component of the complex can be generated by known techniques. For example, such fragments include, but are not limited to, F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed. See, for example, Huse et al., 1989, *Science,* 246: 1275. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques. See, for example, U.S. Pat. No. 4,946,778.

In some embodiments, the antibody or antigen-binding fragment thereof is murine. In some embodiments, the antibody or antigen-binding fragment thereof is from mice. In some embodiments, the antibody or antigen-binding fragment thereof is from rat. In other embodiments, the antibody or antigen binding fragment thereof is human. In some embodiments the antibody or antigen-binding fragment thereof is recombinant, engineered, humanized and/or chimeric.

In some embodiments, an antibody, or antigen binding fragment, variant, or derivative thereof for use in the methods of the invention binds specifically to at least one epitope of target molecule (e.g., a component of the complex, such as S100A9, S100A12, annexin V, annexin VI or PS), i.e., binds to such an epitope more readily than it would bind to an unrelated, or random epitope; binds preferentially to at least one epitope of the target molecule, i.e., binds to such an epitope more readily than it would bind to a related, similar, homologous, or analogous epitope; competitively inhibits binding of a reference antibody which itself binds specifically or preferentially to an epitope of the target molecule; or binds to at least one epitope of the target molecule (e.g., S100A9, S100A12, annexin V, or annexin VI polypeptides or fragments or variants thereof) with an affinity characterized by a dissociation constant Kd of about $5\times10^{-2}$ M, about $10^{-2}$ M, about $5\times10^{-3}$ M, about $10^{-3}$ M, about $5\times10^{-4}$ M, about $10^{-4}$ M, about $5\times10^{-5}$ M, about $10^{-5}$ M, about $5\times10^{-6}$ M, about $10^{-6}$ M, about $5\times10^{-7}$ M, about $10^{-7}$ M, about $5\times10^{-8}$ M, about $10^{-8}$ M, about $5\times10^{-9}$ M, about $10^{-9}$ M, about $5\times10^{-10}$ M, about $10^{-10}$ M, about $5\times10^{-11}$ M, about $10^{-11}$ M, about $5\times10^{-12}$ M, about $10^{-12}$ M, about $5\times10^{-13}$ M, about $10^{-13}$ M, about $5\times10^{-14}$ M, about $10^{-14}$ M, about $5\times10^{-15}$ M, or about $10^{-15}$ M.

In a particular aspect, the antibody or fragment thereof preferentially binds to a human S100A9, S100A12, annexin V, or annexin VI polypeptide or fragment thereof, relative to a murine S100A9, S100A12, annexin V, or annexin VI polypeptide or fragment thereof. As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$M" can include, for example, from 0.05 M to 0.005 M.

In some embodiments, an antibody, or antigen binding fragment, variant, or derivative thereof for use in the methods described herein binds the target molecule (e.g., S100A9, S100A12, annexin V, or annexin VI polypeptides or fragments or variants thereof) with an off rate (k(off)) of less than or equal to about $5\times10^{-2}$ sec$^{-1}$, about $10^{-2}$ sec$^{-1}$, about $5\times10^{-3}$ sec$^{-1}$, about $10^{-3}$ sec$^{-1}$, about $5\times10^{-4}$ sec$^{-1}$, about $10^{-4}$ sec$^{-1}$, about $5\times10$ sec$^{-1}$, about $10^{-4}$ sec$^{-1}$, about $5\times10^{-5}$ sec$^{-1}$, about $10^{-5}$ sec$^{-1}$, about $5\times10^{-6}$ sec$^{-1}$, about $10^{-6}$ sec$^{-1}$, about $5\times10^{-7}$ sec$^{-1}$, or about $10^{-7}$ sec$^{-1}$.

In other embodiments, an antibody, or antigen-binding fragment, variant, or derivative thereof for use in the methods described herein binds the target molecule (e.g., S100A9, S100A12, annexin V, or annexin VI polypeptides or fragments or variants thereof) with an on rate (k(on)) of greater than or equal to about $10^3$ M$^{-1}$sec$^{-1}$, about $5\times10^3$ M$^{-1}$sec$^{-1}$, $10^4$ M$^{-1}$sec$^{-1}$, about $5\times10^4$ M$^{-1}$sec$^{-1}$, $10^5$ M$^{-1}$sec$^{-1}$, about $5\times10^5$ M$^{-1}$sec$^{-1}$, $10^6$ M$^{-1}$sec$^{-1}$, about $5\times10^6$ M$^{-1}$sec$^{-1}$, $10^7$ M$^{-1}$sec$^{-1}$, or about $5\times10^7$ M$^{-1}$sec$^{-1}$.

The binding affinity and dissociation rate of an antibody for use in the methods described herein can be determined by any method known in the art. For example, the binding affinity can be measured by competitive ELISAs, RIAs, BIACORE™, or KINEXA™ technology. The dissociation rate also can be measured by BIACORE™ or KINEXA™ technology. The binding affinity and dissociation rate are measured by surface plasmon resonance using, e.g., a BIACORE™.

In some embodiments, an antibody or an antigen-binding fragment for use in the methods described herein modulates the binding of a first component of the complex with a second component of the complex. In some embodiments, the modulation is enhancement of the binding of the first component of the complex with the second component of the complex. In some embodiments, the modulation is inhibition of the binding of the first component of the complex with the second component of the complex. The IC50 of such inhibition can be measured by any method known in the art, e.g., by ELISA, RIA, or Functional Antagonism. In some embodiments, the IC50 is betWeen 0.1 and 500 nM. In some embodiments, the IC50 is between 10 and 400 nM. In yet other embodiments, the antibody or portion thereof has an IC50 of between 60 nM and 400 nM.

Antibodies for use in the methods of the invention can be generated by immunization of a suitable host (e.g., vertebrates, including humans, mice, rats, sheep, goats, pigs, cattle, horses, reptiles, fishes, amphibians, and in eggs of birds, reptiles and fish). Such antibodies may be polyclonal or monoclonal. In some embodiments, the host is immunized with an immunogenic target molecule (e.g., S100A9, S100A12, annexin V, or annexin VI polypeptides or fragments or variants thereof). In other embodiments, the host is immunized with target molecule (e.g., S100A9, S100A12, annexin V, or annexin VI polypeptides or fragments or variants thereof) associated with a cell membrane of an intact or disrupted cell and antibodies for use in the methods of the invention are identified by binding to the target molecule (e.g., S100A9, S100A12, annexin V, or annexin VI polypeptides or fragments or variants thereof).

In some embodiments, the target molecule (e.g., S100A9, S100A12, annexin V, or annexin VI polypeptides or fragments or variants thereof) antigen is administered with an adjuvant to stimulate the immune response. Adjuvants often need to be administered in addition to antigen in order to elicit an immune response to the antigen. These adjuvants are usually insoluble or undegradable substances that promote nonspecific inflammation, with recruitment of mononuclear phagocytes at the site of immunization. Examples of adjuvants include, but are not limited to, Freund's adjuvant, RIBI (muramyl dipeptides), ISCOM (immunostimulating complexes) or fragments thereof.

For a review of methods for making antibodies, see, e.g., Harlow and Lane, Antibodies, A Laboratory Manual (1988); Yelton, D. E. et al., Ann. Rev. of Biochem. 50:657-80. (1981); and Ausubel et al., Current Protocols in Molecular Biology (New York: John Wiley & Sons) (1989). Determination of immunoreactivity with an immunogenic target molecule (e.g., S100A9, S100A12, annexin V, or annexin VI polypeptides or fragments or variants thereof) antigen can be made by any of several methods well known in the art, including, e.g., immunoblot assay and ELISA.

Without limitations, the antibodies for use in the methods described herein can be of any isotype. An antibody of any desired isotype can be produced by class switching. For class switching, nucleic acids encoding VL or VH, that do not include any nucleotide sequences encoding CL or CH, are isolated using methods well known in the art. The nucleic acids encoding VL or VH are then operatively linked to a nucleotide sequence encoding a CL or CH from a desired class of immunoglobulin molecule. This can be achieved using a vector or nucleic acid that comprises a CL or CH chain, as described above. For example, an antibody for use in the methods described herein that was originally IgM can be class switched to an IgG. Further, the class switching can be used to convert one IgG subclass to another, e.g., from IgG1 to IgG2.

The class and subclass of the antibodies can be determined by any method known in the art. In general, the class and subclass of an antibody can be determined using antibodies that are specific for a particular class and subclass of antibody. Such antibodies are available commercially. The class and subclass can be determined by ELISA, Western Blot, as well as other techniques. Alternatively, the class and subclass can be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

In certain embodiments both the variable and constant regions of the antibodies or immunospecific fragments thereof for use in the treatment methods disclosed herein are fully human. Fully human antibodies can be made using techniques that are known in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140. Other techniques are known in the art. Fully human antibodies can likewise be produced by various display technologies, e.g., phage display or other viral display systems, as described in more detail elsewhere herein.

Antibodies or fragments thereof for use in the treatment methods disclosed herein include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, or derivatization by known protecting/blocking groups, proteolytic cleavage, linkage to a cellular ligand or other protein. Any of numerous chemical modifications may be carried out by known techniques, including, but not limited to, specific chemical cleavage, acetylation, formylation, metabolic synthesis of tunicamycin. Additionally, the derivative may contain one or more non-classical amino acids.

In some embodiments, antibody or fragment thereof for use in the methods disclosed herein will not elicit a deleterious immune response in the mammal to be treated, e.g., in a human. In one embodiment, the antibodies or fragments thereof for use in the methods disclosed herein can be modified to reduce their immunogenicity using art-recognized techniques. For example, antibodies can be humanized, primatized, deimmunized, or chimeric antibodies can be made. These types of antibodies are derived from a nonhuman antibody, typically a murine or primate antibody, that retains or substantially retains the antigen-binding properties of the parent antibody, but which is less immunogenic in humans. This can be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., Proc. Natl. Acad. Sci. USA 81:6851-6855 (1984); Morrison et al., Adv. Immunol. 44:65-92 (1988); Verhoeyen et al., Science 239:15341536 (1988); Padlan, Molec. Immun. 28:489-498 (1991); Padlan, Molec. Immun. 31:169-217 (1994), and U.S. Pat. Nos. 5,585,089; 5,693,761; 5,693,762; and 6,190,370, all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, VH and VL sequences from the starting antibody are analyzed and a human T cell epitope "map" from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of binding polypeptides, e.g., antibodies or immunospecific fragments thereof for use in the methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Completely human antibodies are particularly desirable for therapeutic treatment of human patients. Human antibodies can be made by a variety of methods known in the art including phage display methods using antibody libraries derived from human immunoglobulin sequences. See, for example, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety.

Completely human antibodies, which recognize a selected epitope can be generated using a technique referred to as "guided selection." In this approach a selected nonhuman monoclonal antibody, e.g., a mouse antibody, is used to guide the selection of a completely human antibody recognizing the same epitope. (Jespers et al., Bio/Technology 12:899-903 (1988)). See also, U.S. Pat. No. 5,565,332.

[0162] In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture of antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be produced in relatively large quantities to provide clinical and commercial supplies of the immunoglobulin.

S100A9, also known as calgranulin B and myeloid related protein-14 (MRP-14), is a calcium- and zinc-binding protein that belongs to the S100 protein family. The S100 family of proteins contains 2 EF hand calcium-binding motifs. S100 proteins are localized in the cytoplasm and/or nucleus of a wide range of cells, and involved in the regulation of a number of cellular processes such as cell cycle progression and differentiation. S100 genes include at least 13 members, which are located as a cluster on chromosome 1q21.

S100A9 is highly expressed by the myeloid cell lineage and is found in the extracellular milieu during inflammatory conditions. S100A9 forms heterodimers with S100A8, another member of the S100 family. However, S100A9 can also form monomers, which execute specific functions. In humans, S100A9 is encoded by the S100A9 gene and has a molecular mass of about 13 kDa and is composed of 114 amino acid residues. This protein can function in the inhibition of casein kinase.

Inhibitors of S100 proteins are described, for example in, US Patent Application Publication No. 2007/0231317. Nucleic acid inhibitors of S100A9 (e.g., RNAi molecules, shRNA, and the like) are described for example in U.S. Pat. No. 8,088,751. Antibodies targeting S100A9 are described, for example, in U.S. Pat. No. 7,553,488 and US Patent Application Publication No. 2010/0166775. Content of all the references cited in this paragraph is incorporated herein by reference in its entirety.

Annexins (II, V and VI) are members of a member of a highly conserved protein family, the annexin group that binds acidic phospholipids in a calcium-dependent manner. Annexin-5 possesses a high affinity for phosphatidylserine. Phosphatidylserine is translocated from the inner side of the plasma membrane to the outer layer when cells undergo death by apoptosis or cell necrosis and serves as a signal by which cells destined for death are recognized by phagocytes. Phosphatidylserine (PS) exposure/externalization can occur independently of apoptosis/necrosis; PS has been identified to be constitutively expressed on the surface of macrophages (Callahan M K et al., Cell Death and Differentiation, 2000) and externalization is believed to occur transiently and is not always followed by the death of a cell. The exact function of the protein is unknown; however, annexin A5 has been proposed to play a role in the inhibition of blood coagulation by competing for PS binding sites with prothrombin and also to inhibit the activity of phospholipase A1. These properties have been found by in vitro experiments.

Antibodies against annexin V and VI are available from Abcam (Cambridge, Mass., USA).

PS is a phospholipid component, usually kept on the inner-leaflet (the cytosolic side) of cell membranes by an enzyme called flippase. When a cell undergoes apoptosis or releases matrix vesicles, PS is no longer restricted to the cytosolic part of the membrane, but becomes exposed on the surface of the cell. PS is biosynthesized in the body by condensing the amino acid serine with CDP-activated phosphatidic acid. It is also an important precursor of phosphatidylethanolamine and phosphatidylcholine, although in animals the pathway to generate phosphatidylcholine from phosphatidylserine only operates in the liver.

Sodium ortho-vanadate (Na3VO4), an inhibitor of protein tyrosine phosphatase, induces a rapid and strong inhibition of phosphatidylserine synthesis.

The cell or MV can be contacted with the inhibitor in a cell culture e.g., in vitro or ex vivo, or the inhibitor can be administered to a subject, e.g., in vivo. In some embodiments, the inhibitor can be administered to a subject to decrease, inhibit, prevent, reduce, and/or treat calcification. In some embodiments, the cell is a macrophage.

The term "contacting" or "contact" as used herein in connection with contacting a cell includes subjecting the cells to an appropriate culture media, which comprises the indicated inhibitor. Where the cell is in vivo, "contacting" or "contact" includes administering the inhibitor in a pharmaceutical composition to a subject via an appropriate administration route such that the inhibitor contacts the cell in vivo.

As described herein, the inhibitors can be administered in a pharmaceutically acceptable carrier and can be delivered to the subject's cells in vivo and/or ex vivo by a variety of mechanisms well known in the art.

The term "ex vivo" refers to cells, which are removed from a living organism and cultured outside the organism (e.g., in a test tube). If ex vivo methods are employed, cells or tissues can be removed and maintained outside the body according to standard protocols well known in the art. The compositions can be introduced into the cells via methods known or available to one of skill in the art. For example, the cells can be kept in a culture and inhibitor can be added to the culture media. The treated cells can then be infused (e.g., in a pharmaceutically acceptable carrier) or homotopically transplanted back into the subject per standard methods for the cell or tissue type. Standard methods are known for transplantation or infusion of various cells into a subject.

Generally, any amount of the compound can be contacted with the macrophage. In some embodiments, compound is contacted at a concentration in the range of from about 0.1 nM to about 1000 mM. Preferably the compound is contacted in the range of from about 0.1 µM to about 10 µM.

Additionally, the compound can be contacted with the macrophage for a sufficient time to allow the compound to be taken up by the macrophage and interact with its target. For a non-limiting example, the compound can be contacted with the macrophage for at least 15 minutes before assaying: (i) the release of the MV from the macrophage; (ii) the activity or amount of a component of the complex; or (iii) expression of the nucleic acid encoding a component of the complex.

For administration to a subject, the inhibitor, can be formulated in pharmaceutically acceptable compositions which comprise the inhibitor formulated together with one or more pharmaceutically acceptable carriers (additives) and/or diluents. The inhibitors can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; (9) nasally; or (10) locally via a device or carrier, including but not limited to drug eluting stent or pluronic gel. Additionally, the inhibitors can be implanted into a patient or injected using a drug delivery composition. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (24) $C_2$-$C_{12}$ alcohols, such as ethanol; (25) lipid nanoparticles; and (26) other non-toxic compatible substances employed in pharmaceutical formulations. The carrier or excipient can include time delay material, such as glyceryl monostearate or glyceryl distearate alone or with a wax, or other materials well known in the art. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Pharmaceutically-acceptable antioxidants include, but are not limited to, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acids, and the like.

The preparation of pharmaceutical compositions is well known in the art and has been described in many articles and textbooks, see e.g., Remington's Pharmaceutical Sciences, Gennaro A. R. ed., Mack Publishing Co., Easton, Pa., 1990, content of which of which is incorporated herein by reference in its entirety.

The pharmaceutical compositions can be made up in a solid form (including granules, powders or suppositories) or in a liquid form (e.g., solutions, suspensions, or emulsions). The pharmaceutical compositions can be subjected to conventional pharmaceutical operations such as sterilization and/or can contain conventional adjuvants, such as preservatives, stabilizers, wetting agents, emulsifiers, buffers etc.

Solid dosage forms for oral administration can include capsules, tablets, pills, powders, and granules. In such solid dosage forms, the active compound can be admixed with at least one inert diluent such as sucrose, lactose, or starch. Such dosage forms can also comprise, as in normal practice, additional substances other than inert diluents, e.g., lubricating agents such as magnesium stearate. In the case of capsules, tablets, and pills, the dosage forms can also comprise buffering agents. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting, sweetening, flavoring, and perfuming agents.

For purposes of parenteral administration, solutions in sesame or peanut oil or in aqueous propylene glycol can be employed, as well as sterile aqueous solutions of the corresponding water-soluble salts. Such aqueous solutions can be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art methods of preparing various pharmaceutical compositions with a certain amount of active ingredient are known, or will be apparent in light of this disclosure, to those skilled in this art.

The inhibitors can also be administered in controlled release formulations such as a slow release or a fast release formulation. Such controlled release formulations of the combination of this invention may be prepared using methods well known to those skilled in the art. The method of administration will be determined by the attendant physician or other person skilled in the art after an evaluation of the subject's conditions and requirements.

The amount of inhibitor that can be combined with a carrier material to produce a single dosage form will generally be that amount of the inhibitor that produces a therapeutic effect. Generally out of one hundred percent, this amount will range from about 0.01% to 99% of inhibitor. In some embodiment, amount of the inhibitor in the composition can be selected from the range from about 0.1% to about 99% (w/w), from about 1% to about 90% (w/w), from about 2% to about 80% (w/w), from about 5% to about 75% (w/w), from about 5% to about 50% (w/w), from about 10% (w/w) to about 60% (w/w), from about 0.01% to about 95% (w/v), from about 0.1% to about 90% (w/w), from about 1% to about 85% (w/w), from about 10% to about 50% (w/w), from about 1% to about 99% (w/w), from about 0.05% to about 99% (w/w), from about 0.1% to about 90% (w/w), from about 0.5% to about 85% (w/w), or from about 5% to about 80% (w/w) of the total composition.

In some embodiments, the composition comprises a therapeutically effective amount of the complex inhibitor for the treatment or prevention of cardiovascular calcification.

As used herein, the term "therapeutically effective amount" means an amount of the therapeutic agent which is effective to provide a desired outcome. Determination of a therapeutically effective amount is well within the capability of those skilled in the art. Generally, a therapeutically effective amount can vary with the subject's history, age, condition, sex, as well as the severity and type of the medical condition in the subject, and administration of other agents that inhibit pathological processes in neurodegenerative disorders.

Furthermore, therapeutically effective amounts will vary, as recognized by those skilled in the art, depending on the specific disease treated, the route of administration, the excipient selected, and the possibility of combination therapy. In some embodiments, the therapeutically effective amount can be in a range between the $ED_{50}$ and $LD_{50}$ (a dose of a therapeutic agent at which about 50% of subjects taking it are killed). In some embodiments, the therapeutically effective amount can be in a range between the $ED_{50}$ (a dose of a therapeutic agent at which a therapeutic effect is detected in at least about 50% of subjects taking it) and the $TD_{50}$ (a dose at which toxicity occurs at about 50% of the cases). Guidance regarding the efficacy and dosage which will deliver a therapeutically effective amount of a compound can be obtained from animal models of condition to be treated.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the $IC_{50}$ (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay. Examples of suitable bioassays include DNA replication assays, transcription based assays, and immunological assays.

The dosage can be determined by a physician and adjusted, as necessary, to suit observed effects of the treatment. Generally, the complex inhibitors are administered so that the inhibitor is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 tmg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like. For protein based inhibitors (such as antibodies) one preferred dosage is 0.1 mg/kg to 100 mg/kg of body weight (generally 10 mg/kg to 20 mg/kg).

As used herein, the term "administer" refers to the placement of a composition into a subject by a method or route, which results in at least partial localization of the pharmaceutically active agent at a desired site. The inhibitors can be administered in any suitable manner. The manner of administration can be chosen based on, for example, whether local or systemic treatment is desired, and on the area to be treated. Accordingly, a composition can be administered by any appropriate route, which results in effective treatment in the subject, i.e., administration results in delivery to a desired location in the subject where at least a portion of the pharmaceutically active agent is delivered. Exemplary modes of administration include, but are not limited to, implant, injection, infusion, instillation, implantation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

In some embodiments, a composition described herein can be implanted in a subject. As used herein, the term "implanted," and grammatically related terms, refers to the positioning of the composition in a particular locus in the subject, either temporarily, semi-permanently, or permanently. The term does not require a permanent fixation of the composition in a particular position or location.

With respect to duration and frequency of administration or treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration once a month, once every two week, once a week, once every other day, daily, twice daily, three times daily or four or more times daily over a period of 1 week, 2 weeks, 3 weeks, 4 weeks, 1 month, 2 months, 3 months, 4 months, 5 months, or 6 months or more.

In some embodiments, the inhibitor can be co-administered to the subject with in combination with a pharmaceutically active agent or therapeutic agent. Without limitations, the inhibitor can be administered before, concurrently, or after administration of the therapeutic agent. Thus, as used herein, the term "co-administer" refers to administration of two or more agents (e.g., the inhibitor and the pharmaceutically active agent) within a 24 hour period of each other, for example, as part of a clinical treatment regimen. In other embodiments, "co-administer" refers to administration within 12 hours, within 6 hours, within 5 hours, within 4 hours, within 3 hours, within 2 hours, within 1 hour, within 45, within 30 minutes, within 20, within 15 minutes, within 10 minutes, or within 5 minutes of each other. In other embodiments, "co-administer" refers to administration at the same time, either as part of a single formulation or as multiple formulations that are administered by the same or different routes. When the inhibitor and the pharmaceutically active agent are administered in different pharmaceutical compositions or at different times, routes of administration can be same or different.

Exemplary pharmaceutically active compound include, but are not limited to, those found in Harrison's Principles of Internal Medicine, 13$^{th}$ Edition, Eds. T. R. Harrison et al. McGraw-Hill N.Y., NY; Physicians' Desk Reference, 50$^{th}$ Edition, 1997, Oradell N.J., Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's The Pharmacological Basis of Therapeutics; and current edition of The Merck Index, the complete contents of all of which are incorporated herein by reference.

In some embodiments, pharmaceutically active agent can include those agents known in the art for treating vascular calcification, such as vitamin D sterols and/or RENAGEL®. Vitamin D sterols can include calcitriol, alfacalcidol, doxercalciferol, maxacalcitol or paricalcitol.

In some embodiments, pharmaceutically active agent can include calcimimetics, vitamins and their analogs, antibiotics, lanthanum carbonate, lipid-lowering agents, such as LIPITOR®, other modulators for lipid profile (e.g., HDL-raising drugs), anti-hypertensives, anti-inflammatory agents (steroidal and non-steroidal), inhibitors of pro-inflammatory cytokine (ENBRELOR®, KINERET®), and cardiovascular agents.

In some embodiments, pharmaceutically active agent can be a statin.

In some embodiments, pharmaceutically active agent includes those agents known in the art for treatment of inflammation or inflammation associated disorders.

In some embodiments, the pharmaceutically active agent is an anti-inflammatory agent. Exemplary anti-inflammatory agents include, but are not limited to, non-steroidal anti-inflammatory drugs (NSAIDs—such as aspirin, ibuprofen, or naproxen, coricosteroids (such as presnisone), anti-malarial medication (such as hydrochloroquine), methotrexrate, sulfasalazine, leflunomide, anti-TNF medications, cyclophosphamise and mycophenolate.

In some embodiments, the pharmaceutically active agent is a immune response modulator. As used herein, the term "immune response modulator" refers to compound (e.g., a small-molecule, antibody, peptide, nucleic acid, or gene therapy reagent) that inhibits autoimmune response in a subject. Without wishing to be bound by theory, an immune response modulator inhibits the autoimmune response by inhibiting the activity, activation, or expression of inflammatory cytokines (e.g., IL-12, IL-23 or IL-27), or STAT-4. Exemplary immune response modulators include, but are not limited to, members of the group consisting of Lisofylline (LSF) and the LSF analogs and derivatives described in U.S. Pat. No. 6,774,130, contents of which are herein incorporated by reference in their entirety.

In some embodiments, the pharmaceutically active agent is an antibiotic agent. The term "antibiotic" is used herein to describe a compound or composition which decreases the viability of a microorganism, or which inhibits the growth or reproduction of a microorganism. As used in this disclosure, an antibiotic is further intended to include an antimicrobial, bacteriostatic, or bactericidal agent. Exemplary antibiotics include, but are not limited to, penicillins, cephalosporins, penems, carbapenems, monobactams, aminoglycosides, sulfonamides, macrolides, tetracyclins, lincosides, quinolones, chloramphenicol, vancomycin, metronidazole, rifampin, isoniazid, spectinomycin, trimethoprim, sulfamethoxazole, and the like.

The dosage regimen for treating a disease condition with the combination therapy disclosed herein can be selected in accordance with a variety of factors, including the type, age, weight, sex and medical condition of the patient, the severity of the disease, the route of administration, and the particular compound employed, and thus can vary widely.

In some embodiments, the inhibitor can be administered in conjunction with surgical and non-surgical treatments. In some embodiments, the methods disclosed herein can be practiced in injunction with dialysis.

Cardiovascular calcification, a well-recognized and common complication of CRD (also known as chronic kidney disease (CKD)), increases the risk of cardiovascular morbidity and mortality (Giachelli, C. J. Am. Soc. Nephrol. 15: 2959-64, 2004; Raggi, P. et al. J. Am. Coll. Cardiol. 39: 695-701, 2002). While the causes of cardiovascular calcification in CKD remain to be elucidated, associated risk factors include age, gender, hypertension, time on dialysis, diabetes and glucose intolerance, obesity, dyslipidemia, and cigarette smoking (Zoccali C. Nephrol. Dial. Transplant 15: 454-7, 2000). These conventional risk factors, however, do not adequately explain the high mortality rates from cardiovascular causes in the patient population. Recent observations suggest that certain abnormalities in calcium and phosphorus metabolism, a mineral imbalance, resulting in a raised serum calcium-phosphorus product contribute to the development of arterial calcification, and possibly to cardiovascular disease, in patients with end-stage renal disease (Goodman, W. et al. N. Engl. J. Med. 342: 1478-83, 2000; Guérin, A. et al. Nephrol. Dial. Transplant 15: 1014-21, 2000; Vattikuti, R. & Towler, D. Am. J. Physiol. Endocrinol. Metab. 286: E686-96, 2004).

Another hallmark of advanced CKD is secondary hyperparathyroidism (HPT), characterized by elevated parathyroid hormone (PTH) levels and disordered mineral metabolism. The elevations in calcium, phosphorus, and CaxP observed in patients with secondary HPT have been associated with an increased risk of vascular calcification (ChertoW, G. et al. Kidney Int. 62: 245-52, 2002; Goodman, W. et al. N. Engl. J. Med. 342: 1478-83, 2000; Raggi, P. et al. J. Am. Coll. Cardiol. 39: 695-701, 2002). Commonly used therapeutic interventions for secondary HPT, such as calcium-based phosphate binders and doses of active vitamin D sterols can result in hypercalcemia and hyperphosphatemia (ChertoW, G. et al. Kidney Int. 62: 245-52, 2002; Tan, A. et al. Kidney Int 51: 317-23, 1997; Gallieni, M. et al. Kidney Int 42: 1191-8, 1992), which are associated with the development or exacerbation of vascular calcification.

Vascular calcification is an important and potentially serious complication of chronic renal failure. Two distinct patterns of vascular calcification have been identified (Proudfoot, D & Shanahan, C. Herz 26: 245-51, 2001), and it is common for both types to be present in uremic patients (Chen, N. & Moe, S. Semin Nephrol 24: 61-8, 2004). Medial calcification occurs in the media of the vessel in conjunction with a phenotypic transformation of smooth muscle cells into osteoblast-like cells, while atherogenesis is associated with lipid-laden macrophages and intimal hyperplasia.

Medial wall calcification can develop in relatively young persons with chronic renal failure, and it is common in patients with diabetes mellitus even in the absence of renal disease. The presence of calcium in the medial wall of arteries distinguishes this type of vascular calcification from that associated with atherosclerosis (Schinke T. & Karsenty G. Nephrol Dial Transplant 15: 1272-4, 2000). Atherosclerotic vascular calcification occurs in atheromatous plaques along the intimal layer of arteries (Farzaneh-Far A. JAMA 284:1515-6, 2000). Calcification is usually greatest in large, well developed lesions, and it increases with age (Wexler L. et al. Circulation 94: 1175-92, 1996; Rumberger J. et al. Mayo Clin Proc 1999; 74: 243-52). The extent of arterial calcification in patients with atherosclerosis generally corresponds to severity of disease. Unlike medial wall calcification, atherosclerotic vascular lesions, whether or not they contain calcium, impinge upon the arterial lumen and compromise blood flow. The localized deposition of calcium within atherosclerotic plaques may happen because of inflammation due to oxidized lipids and other oxidative stresses and infiltration by monocytes and macrophages (Berliner J. et al. Circulation 91: 2488-96, 1995). In addition, arterial microcalcifications in the thin cap overlying the necrotic core in the intima of atherosclerotic plaques may cause compliance mismatch, increase local stress, and promote microfractures—leading to plaque rupture causing acute cardiovascular events (Libby P, Aikawa M. *Nat Med.;* 8:1257-62, 2002). Atherosclerotic plaques containing "spotty" calcifications consisting of calcified vesicles (precursors to microcalcification) have increased stress, thus making them more susceptible to rupture (Wenk J F, *J Biomech Eng.;* 132:091011, 2010).

Some patients with end-stage renal disease develop a severe form of occlusive arterial disease called calciphylaxis or calcific uremic arteriolopathy. This syndrome is characterized by extensive calcium deposition in small arteries (Gipstein R. et al. Arch Intern Med 136: 1273-80, 1976; Richens G. et al. J Am Acad. Dermatol. 6: 537-9, 1982). In patients with this disease, arterial calcification and vascular occlusion lead to tissue ischemia and necrosis. Involvement of peripheral vessels can cause ulceration of the skin of the lower legs or gangrene of the digits of the feet or hands. Ischemia and necrosis of the skin and subcutaneous adipose tissue of the abdominal Wall, thighs and/or buttocks are features of a proximal form of calcific uremic arteriolopathy (Budisavljevic M. et al. J Am Soc Nephrol. 7: 978-82, 1996; Ruggian J. et al. Am. J. Kidney Dis. 28: 409-14, 1996). This syndrome occurs more frequently in obese individuals, and women are affected more often than men for reasons that remain unclear (Goodman W. J. Nephrol. 15 (6): S82-S85, 2002).

As used herein, the term "vascular calcification" means formation, growth or deposition of extracellular matrix hydroxyapatite (calcium phosphate) crystal deposits in blood vessels. Vascular calcification encompasses coronary, valvular, aortic, arterial, and other blood vessel calcification. The term includes atherosclerotic and medial wall calcification.

As used herein, the term "atherosclerotic calcification" means vascular calcification occurring in atheromatous plaques along the intimal layer of arteries.

Intimal calcification occurs within the perimeter of the internal elastic lamina as part of the atherosclerotic plaque and is often seen as discrete, punctuate lesions on radiographs. It is associated with inflammatory cells, lipid, and vascular smooth muscle cells.

As used herein, the terms "medial calcification," "medial wall calcification," and "Monckeberg's sclerosis," mean calcification characterized by the presence of calcium in the medial wall of arteries.

Cardiovascular calcification includes valvular calcification such as aortic valve calcification that leads to aortic stenosis and heart failure.

Methods of detecting and measuring cardiovascular calcification are well known in the art. In one aspect, methods of measuring calcification include direct methods of detecting and measuring extent of calcium-phosphorus depositions in blood vessels.

In one aspect, direct methods of measuring cardiovascular calcification comprise in vivo imaging methods such as plain film roentgenography, coronary arteriography; fluoroscopy, including digital subtraction fluoroscopy; cinefluorography; conventional, helical, and electron beam computed tomography; intravascular ultrasound (IVUS); magnetic resonance imaging; and transthoracic and transesophageal echocardiography. Fluoroscopy and EBCT are most commonly used to detect calcification noninvasively, while cinefluorography and IVUS are used by coronary interventionalists to evaluate calcification in specific lesions before angioplasty. Transthoracic echocardiography is commonly used to detect aortic valve calcification.

In one aspect, cardiovascular calcification can be detected by plain film roentgenography. The advantage of this method is availability of the film and the low cost of the method, however, the disadvantage is its low sensitivity. Kelley M. & Newell J. Cardiol Clin. 1: 575-595, 1983.

In another aspect, fluoroscopy can be used to detect calcification in coronary arteries. Although fluoroscopy can detect moderate to large calcifications, its ability to identify small calcific deposits is low. Loecker et al. J Am Coll Cardiol. 19: 1167-1172, 1992. Fluoroscopy is widely available in both inpatient and outpatient settings and is relatively inexpensive, but it has several disadvantages. In addition to only a low to moderate sensitivity, fluoroscopic detection of calcium is dependent on the skill and experience of the operator as well as the number of views studied. Other important factors include variability of fluoroscopic equipment, the patient's body habitus, overlying anatomic structures, and overlying calcifications in structures such as vertebrae and valve annuli. With fluoroscopy, quantification of calcium is not possible, and film documentation is not commonly obtained.

In yet another aspect, cardiovascular detection can be detected by conventional computed tomography (CT). Because calcium attenuates the x-ray beam, computed tomography (CT) is extremely sensitive in detecting vascular calcification. While conventional CT appears to have better capability than fluoroscopy to detect coronary artery calcification, its limitations are slow scan times resulting in motion artifacts, volume averaging, breathing misregistration, and inability to quantify amount of plaque. Wexler et al. Circulation 94: 1175-1192, 1996. Aortic valve calcification is often detected by conventional CT, particularly in the elderly (Liu et al., American Journal of Roentgenology 186:342-349, 2006).

In a further aspect, calcification can be detected by helical or spiral computer tomography, which has considerably faster scan times than conventional CT. Overlapping sections also improve calcium detection. Shemesh et al. reported coronary calcium imaging by helical CT as having a sensitivity of 91% and a specificity of 52% when compared with angiographically significant coronary obstructive disease. Shemesh et al. Radiology 197: 779-783, 1995. However, other preliminary data have shown that even at these accelerated scan times, and especially with single helical CT, calcific deposits are blurred due to cardiac motion, and small calcifications may not be seen. Baskin et al. Circulation 92 (suppl I): 1-651, 1995. Thus, helical CT remains superior to fluoroscopy and conventional CT in detecting calcification. Double-helix CT scanners appear to be more sensitive than single-helix scanners in detection of coronary calcification because of their higher resolution and thinner slice capabilities. Wexler et al., supra.

In another aspect, Electron Beam Computed Tomography (EBCT) can be used for detection of cardiovascular calcification. EBCT uses an electron gun and a stationary tungsten "target" rather than a standard x-ray tube to generate x-rays, permitting very rapid scanning times. Originally referred to as cine or ultrafast CT, the term EBCT is now used to distinguish it from standard CT scans because modern spiral scanners are also achieving subsecond scanning times. For purposes of detecting coronary calcium, EBCT images are obtained in 100 ms with a scan slice thickness of 3 mm. Thirty to 40 adjacent axial scans are obtained by table incrementation. The scans, which are usually acquired during one or two separate breath-holding sequences, are triggered by the electrocardiographic signal at 80% of the RR interval, near the end of diastole and before atrial contraction, to minimize the effect of cardiac motion. The rapid image acquisition time virtually eliminates motion artifact related to cardiac contraction. The unopacified coronary arteries are easily identified by EBCT because the lower CT density of periarterial fat produces marked contrast to blood in the coronary arteries, while the mural calcium is evident because of its high CT density relative to blood. Additionally, the scanner software allows quantification of calcium area and density. An arbitrary scoring system has been devised based on the x-ray attenuation coefficient, or CT number measured in Hounsfield units, and the area of calcified deposits. Agatston et al. J Am Coll Cardiol. 15:827832, 1990. A screening study for coronary calcium can be completed within 10 or 15 minutes, requiring only a few seconds of scanning time. Electron beam CT scanners are more expensive than conventional or spiral CT scanners and are available in relatively fewer sites.

In one aspect, intravascular ultrasound (IVUS) can be used for detecting vascular calcification, in particular, coronary atherosclerosis. Waller et al. Circulation 85: 23052310, 1992. By using transducers with rotating reflectors mounted on the tips of catheters, it is possible to obtain cross-sectional images of the coronary arteries during cardiac catheterization. The sonograms provide information not only about the lumen of the artery but also about the thickness and tissue characteristics of the arterial wall. Calcification is seen as a hyperechoic area with shadowing: fibrotic noncalcified plaques are seen as hyperechoic areas without shadowing. Honye et al. Trends Cardiovasc Med. 1: 305-311, 1991. The disadvantages in use of IVUS, as opposed to other imaging modalities, are that it is invasive and currently performed only in conjunction with selective coronary angiography, and it visualizes only a limited portion of the coronary tree. Although invasive, the technique is clinically important because it can show atherosclerotic involvement in patients with normal findings on coronary arteriograms and helps define the morphological characteristics of stenotic lesions before balloon angioplasty and selection of atherectomy devices. Tuzcu et al. J Am Coll Cardiol. 27: 832-838, 1996.

In another aspect, cardiovascular calcification can be measured by magnetic resonance imaging (MRI). However, the ability of MRI to detect coronary calcification is somewhat limited. Because microcalcifications do not substantially alter the signal intensity of voxels that contain a large amount of soft tissue, the net contrast in such calcium collections is low. Therefore, MRI detection of small quantities of calcification is difficult, and there are no reports or expected roles for MRI in detection of early coronary artery calcification or microcalcification. Wexler et al., supra.

In another aspect, cardiovascular calcification can be measured by transthoracic (surface) echocardiography, which is particularly sensitive to detection of mitral and aortic valvular calcification; however, visualization of the coronary arteries has been documented only on rare occasions because of the limited available external acoustic windows. Transesophageal echocardiography is a widely available methodology that often can visualize the proximal coronary arteries (Koh et al. Int J Cardiol. 43: 202-206, 1994. Fernandes et al. Circulation 88: 2532-2540, 1993).

In another aspect, vascular calcification can be assessed using near-infrared molecular imaging with a sensitive calcium binding molecular imaging agent using intravital fluorescence microscope or fluorescence reflectance imaging system (Aikawa E et al 116: 2841-2850, Circulation, 2007; Aikawa E et al, 119: 1785-1794; Circulation, 2009; New E P et al. 108; 1381-1391, Circ Res, 2011). However, while molecular imaging provides high-resolution images of microcalcification, the system has been used only for animal studies.

In another aspect, cardiovascular calcification can be assessed in humans using 18F-Sodium Fluoride (18F—NaF) Positron Emission Tomography (PET) (George et al., J Am Coll Cardiol. 59:1549-50, 2012; Dweck et al., J Am Coll Cardiol. 59:1539-1548, 2012; Aikawa E, et al., Circulation 125:9-11, 2012; Dweck et al., Circulation 125:76-86, 2012).

In another aspect, vascular calcification can be assessed ex vivo by Van Kossa method. This method relies upon the principle that silver ions can be displaced from solution by carbonate or phosphate ions due to their respective positions in the electrochemical series. The argentaffin reaction is photochemical in nature and the activation energy is supplied from strong visible or ultra-violet light. Since the demonstrable forms of tissue carbonate or phosphate ions are invariably associated with calcium ions the method may be considered as demonstrating sites of tissue calcium deposition.

Other methods of direct measuring calcification may include, but not limited to, immunofluorescent staining and densitometry. In another aspect, methods of assessing vascular calcification include methods of measuring determinants and/or risk factors of vascular calcification. Such factors include, but are not limited to, serum levels of phosphorus, calcium, and calciumxphosphorus product, parathyroid hormone (PTH), low-density lipoprotein cholesterol (LDL), high-density lipoprotein cholesterol (HDL), triglycerides, and creatinine. Methods of measuring these factors are well known in the art. Other methods of assessing vascular calcification include assessing factors of bone formation. Such factors include bone formation markers such as bone-specific alkaline phosphatase (BSAP), osteocalcin (OC), carboxyterminal propeptide of type I collagen (PICP), and amino terminal propeptide of type I collagen (PINP); serum bone resorption markers such as cross-linked C-telopeptide of type I collagen (ICTP), tartrate-resistant acid phosphatase, TRACP and TRAP5B, N-telopeptide of collagen cross-links (NTx), and C-telopeptide of collagen cross-links (CTx); and urine bone resorption markers, such as hydroxyproline, free and total pyridinolines (Pyd), free and total deoxypyridinolines (Dpd), N-telopeptide of collagen cross-links (NTx), and C-telopeptide of collagen cross-links (CTx).

Exemplary embodiments of the invention can be described by any one of the following numbered paragraphs:
1. A method for inhibiting calcification of a macrophage derived matrix vesicle (MV), the method comprising contacting a macrophage with a compound, wherein the compound inhibits: (i) release of the matrix vesicle from the macrophage or SMC or interstitial valvular cell; (ii) amount or formation of a complex comprising phosphatidylserine (PS), annexin II, V or VI, and S100A9 or S100A12 in the matrix vesicle or the macrophage; or (iii) expression level of a nucleic acid encoding annexin II, annexin V, annexin VI, S100A9, or S100A12 in the macrophage.
2. The method of paragraph 1, wherein the complex comprises PS, annexin V, and S100A9.
3. The method of paragraph 1 or 2, the compound is selected from the group consisting of small organic or inorganic molecules; saccharines; oligosaccharides; polysaccharides; peptides; proteins; peptide analogs and derivatives; peptidomimetics; glycoproteins, glycopeptides; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof
4. The method of any of paragraphs 1-3, wherein the compound is an siRNA or an antibody.
5. The method of any of paragraphs 1-4, wherein the compound inhibits release of the matrix vesicle from the macrophage by at least 10% relative to a control or reference level.
6. The method of any of paragraphs 1-5, wherein the compound inhibits complexation/binding of S100A9 or S100A12 with at least one of annexin II, annexin V, annexin VI and PS by at least 10% relative to a control or reference level.
7. The method of any of paragraphs 1-6, wherein the compound inhibits complexation/binding of annexin II, annexin V or annexin VI with at least one of S100A9, S100A12, and PS by at least 10% relative to a control or reference level.
8. The method of any of paragraphs 1-7, wherein the compound inhibits complexation/binding of PS with at least one of annexin II, annexin V, annexin VI, S100A9 and S100A12 by at least 10% % relative to a control or reference level.
9. The method of any of paragraphs 1-8, wherein the compound reduces the amount of the complex in the matrix vesicle or macrophage by at least 10% relative to control or reference level.
10. The method of any of paragraphs 1-9, wherein the compound reduces the amount of at least one of PS, annexin II, annexin V, annexin VI, S100A9 and S100A12 in the matrix vesicle or the macrophage by at least 10% relative to a control or reference level.
11. The method of any of paragraphs 1-10, wherein the compound inhibits the expression of the nucleic acid encoding annexin II, annexin V, annexin VI, S100A9, or S100A12 in the macrophage by at least 10% relative to a control or reference level.
12. The method of any of paragraphs 1-11, wherein the nucleic acid encoding S100A9, S100A12, annexin II, annexin V or annexin VI is an mRNA.
13. The method of any of paragraphs 1-12, wherein said contacting is in vitro.
14. The method of any of paragraphs 1-13, wherein said contacting is in vivo.
15. The method of paragraph 14, wherein said contacting is in a mammal.
16. The method of paragraph 14 or 15, wherein said contacting is in a subject in need of inhibition of calcification.
17. The method of paragraph 16, wherein said calcification is cardiovascular calcification.
18. The method of paragraph 16 or 17, wherein said calcification is valvular or arterial calcification.
19. The method of any of paragraphs 16-18, wherein the subject has severe renal failure or has a transcatheter aortic valve implantation or chronic coronary atherosclerosis or aortic stenosis.
20. The method of any of paragraphs 16-19, wherein the subject has mineral imbalance or a calcium/phosphate disorder, including chronic renal disease, hemodyalysis and type II diabetes; arterio-venous grafts/shunts; arterial and vein grafts; tissue engineered vascular and valvular implants; Paget's disease, rheumatoid arthritis, osteoporosis or osteoarthritis.
21. A method for inhibiting calcification or a clinical complication arising therefrom in a subject, the method comprising administering a therapeutically effective amount of a compound to a subject in need thereof, wherein the compound inhibits: (i) release of a matrix vesicle from a macrophage, SMC, or interstitial valvular cell; (ii) amount or formation of the complex comprising phosphatidylserine (PS), annexin II, annexin V or VI, and S100A9 or S100A12 in the matrix vesicle or the macrophage, SMC, or interstitial valvular cell; or (iii) expression level of a nucleic acid encoding annexin II, annexin V, annexin VI, S100A9, or S100A12 in the macrophage SMC, or interstitial valvular cell.
22. The method of paragraph 21, wherein the complex comprises PS, annexin V/VI, and S100A9.
23. The method of paragraph 21 or 22, the compound is selected from the group consisting of small organic or inorganic molecules; saccharines; oligosaccharides; polysaccharides; peptides; proteins; peptide analogs and derivatives; peptidomimetics; glycoproteins, glycopeptides; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof
24. The method of any of paragraphs 21-23, wherein the compound is an siRNA or an antibody.
25. The method of any of paragraphs 21-24, wherein the compound inhibits release of the matrix vesicle from the macrophage by at least 10% relative to a control or reference level.
26. The method of any of paragraphs 21-25, wherein the compound inhibits complexation/binding of S100A9 or S100A12 with at least one of annexin II, annexin V, annexin VI and PS by at least 10% relative to a control or reference level.
27. The method of any of paragraphs 21-26, wherein the compound inhibits complexation/binding of annexin II, annexin V or annexin VI with at least one of S100A9, S100A12, and PS by at least 10% relative to a control or reference level.
28. The method of any of paragraphs 21-27, wherein the compound inhibits complexation of PS with at least one of annexin II, annexin V, annexin VI, S100A9 and S100A12 by at least 10% % relative to a control or reference level.
29. The method of any of paragraphs 21-28, wherein the compound reduces the amount of the complex in the matrix vesicle or macrophage by at least 10% relative to control or reference level.
30. The method of any of paragraphs 21-29, wherein the compound reduces the amount of at least one of PS, annexin V, annexin VI, S100A9 and S100A12 in the matrix vesicle or the macrophage by at least 10% relative to a control or reference level.
31. The method of any of paragraphs 21-30, wherein the compound inhibits the expression of the nucleic acid encoding annexin II, annexin V, annexin VI, S100A9, or S100A12 in the macrophage by at least 10% relative to a control or reference level.
32. The method of any of paragraphs 21-31, wherein the nucleic acid is mRNA.
33. The method of any of paragraphs 21-32, wherein said administering is implant, injection, infusion, instillation, implantation, or ingestion
34. The method of any of paragraphs 21-33, wherein the therapeutically effective amount is from about 1 µg/kg to about 150 mg/kg of body weight.
35. The method of any of paragraphs 21-34, wherein said administering is once a day.
36. The method of any of paragraphs 21-35, wherein the subject is a mammal.
37. The method of any of paragraphs 21-36, wherein said calcification is cardio vascular calcification.
38. The method of any of paragraphs 21-37, wherein said calcification is valvular or arterial calcification.
39. The method of any of paragraphs 21-38, wherein the subject has severe renal failure or has a transcatheter aortic valve implantation or chronic coronary atherosclerosis or aortic stenosis.
40. The method of any of paragraphs 21-39, wherein the subject has mineral imbalance or a calcium/phosphate disorder, including chronic renal disease, hemodyalysis and type II diabetes; arterio-venous grafts/shunts; arterial and vein grafts; tissue engineered vascular and valvular implants; Paget's disease, rheumatoid arthritis, osteoporosis or osteoarthritis.
41. The method of any of paragraphs 21-40, wherein the clinical complication is acute myocardial infraction, stroke, and the like.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used interchangeably herein, the terms "essentially" and "substantially" means a proportion of at least about 60%, or preferably at least about 70% or at least about 80%, or at least about 90%, at least about 95%, at least about 97% or at least about 99% or more, or any integer between 70% and 100%. In some embodiments, the term "essentially" means a proportion of at least about 90%, at least about 95%, at least about 98%, at least about 99% or more, or any integer between 90% and 100%. In some embodiments, the term "essentially" can include 100%.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

As used herein, the term "subject" is intended to mean a human or other mammal, exhibiting, or at risk of developing, calcification. Such an individual can have, or be at risk of developing, for example, vascular calcification associated with conditions such as atherosclerosis, stenosis, restenosis, renal failure, diabetes, prosthesis implantation, tissue injury or age-related vascular disease. The prognostic and clinical indications of these conditions are known in the art. An individual treated by a method of the invention can have a systemic mineral imbalance associated with, for example, diabetes, chronic kidney disease, renal failure, kidney transplantation or kidney dialysis.

The subject can be initially diagnosed by a licensed physician and/or authorized medical practitioner, and a regimen for prophylactic and/or therapeutic treatment via a method described herein can be suggested, recommended or prescribed. Thus, in some embodiments, the method comprises selecting a subject for treatment for vascular calcification.

Animal models that are reliable indicators of human atherosclerosis, renal failure, hyperphosphatemia, diabetes, age-related vascular calcification and other conditions associated with vascular calcification are known in the art. For example, an experimental model of calcification of the vessel wall is described by Yamaguchi et al., Exp. Path. 25: 185-190, 1984, content of which is incorporated herein by reference in its entirety.

By "treatment, prevention or amelioration" is meant delaying or preventing the onset of a disorder or reversing, alleviating, ameliorating, inhibiting, slowing down or stopping the progression, aggravation or deterioration the progression or severity of a condition. In some embodiments, at least one symptom is alleviated by at least 20%, at least 30%, at least 40%, at least 50%, at least 60%, at least 70%, at least 80%, at least 90%, or at least 95% but not 100%, i.e. not a complete alleviation. In some embodiments, at least one symptom is completely alleviated.

As used herein, the terms "inhibiting," "decreasing," "preventing," and "treating" in connection with vascular calcification, are intended to mean preventing, retarding, or reversing formation, growth or deposition of extracellular matrix hydroxyapatite crystal deposits. Without limitations, the improvement in disorder severity includes the reversal of vascular calcification, as well as slowing down the progression of vascular calcification.

As used herein, the terms "proteins" and "peptides" are used interchangeably herein to designate a series of amino acid residues connected to the other by peptide bonds between the alpha-amino and carboxy groups of adjacent residues. The terms "protein", and "peptide", which are used interchangeably herein, refer to a polymer of protein amino acids, including modified amino acids (e.g., phosphorylated, glycated, etc.) and amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein" and "peptide" are used interchangeably herein when referring to a gene product and fragments thereof. Thus, exemplary peptides or proteins include gene products, naturally occurring proteins, homologs, orthologs, paralogs, fragments and other equivalents, variants, fragments, and analogs of the foregoing.

As used herein, the term "peptidomimetic" refers to a molecule that folds into or has a defined three-dimensional structure similar to a natural peptide.

The term "heavy chain" includes a full-length heavy chain and fragments thereof having sufficient variable region sequence to confer specificity for a component of the complex, e.g., PS, annexin II, annexin V, annexin VI, S100A9, or S100A12. A full-length heavy chain includes a variable region domain, VH, and three constant region domains, CH1, CH2, and CH3. The VH domain is at the amino-terminus of the polypeptide, and the CH3 domain is at the carboxyl-terminus.

The term "light chain" includes a full-length light chain and fragments thereof having sufficient variable region sequence to confer specificity for a component of the complex, e.g., PS, annexin II, annexin V, annexin VI, S100A9, or S100A12. A full-length light chain includes a variable region domain, VL, and a constant region domain, CL. Like the heavy chain, the variable region domain of the light chain is at the amino-terminus of the polypeptide.

A "Fab fragment" is comprised of one light chain and the CHI and variable regions of one heavy chain. The heavy chain of a Fab molecule cannot form a disulfide bond with another heavy chain molecule.

A "Fab' fragment" contains one light chain and one heavy chain that contains more of the constant region, between the CH1 and CH2 domains, such that an interchain disulfide bond can be formed between two heavy chains to form a F(ab')2 molecule.

A "F(ab')$_2$ fragment" contains two light chains and two heavy chains containing a portion of the constant region between the CH1 and CH2 domains, such that an interchain disulfide bond is formed between two heavy chains.

The "Fv region" comprises the variable regions from both the heavy and light chains, but lacks the constant regions.

As used herein, the term "Complementarity Determining Regions" (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203 (hereby incorporated by reference).

The expression "linear antibodies" refers to the antibodies described in Zapata et al., Protein Eng., 8(10):1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

The expression "single-chain Fv" or "scFv" antibody fragments, as used herein, is intended to mean antibody fragments that comprise the VH and VL domains of antibody, wherein these domains are present in a single polypeptide chain. Preferably, the Fv polypeptide further comprises a polypeptide linker between the VH and VL domains which enables the scFv to form the desired structure for antigen binding. (The Pharmacology of Monoclonal Antibodies, vol. 113, Rosenburg and Moore eds., Springer-Verlag, New York, pp. 269-315 (1994)).

The term "diabodies," as used herein, refers to small antibody fragments with two antigen-binding sites, which fragments comprise a heavy-chain variable domain (VH) Connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. (EP 404,097; WO 93/11161; Hollinger et ah, Proc. Natl. Acad. Sd. USA, P0:6444-6448 (1993)).

A "bivalent antibody" other than a "multispecific" or "multifunctional" antibody, in certain embodiments, is understood to comprise binding sites having identical antigenic specificity.

A "bispecific" or "bifunctional" antibody is a hybrid antibody having two different heavy/light chain pairs and two different binding sites. Bispecific antibodies may be produced by a variety of methods including, but not limited to, fusion of hybridomas or linking of Fab' fragments. See, e.g., Songsivilai & Lachmann (1990), Clin. Exp. Immunol. 79:315-321; Kostelny et al. (1992), J. Immunol. 148: 15471553.

As used herein, the term "humanized antibody" means an antibody in which at least a portion of non-human sequences are replaced with human sequences. Examples of how to make humanized antibodies can be found, for example, in U.S. Pat. No. 6,054,297; No. 5,886,152; and U.S. Pat. No. 5,877,293, content of all of which is incorporated herein by reference in its entirety.

As used herein, the term "chimeric antibody" means an antibody that contains one or more regions from a first antibody and one or more regions from at least one other antibody. The first antibody and the additional antibodies can be from the same or different species.

As used herein, the term "antigens" refers to a molecule or a portion of a molecule capable of being bound by a selective binding agent, such as an antibody, and additionally capable of being used in an animal to elicit the production of antibodies capable of binding to an epitope of that antigen. An antigen may have one or more epitopes. The term "antigen" can also refer to a molecule capable of being bound by an antibody.

As used herein, the term "polysaccharide" refers to macromolecular carbohydrates whose molecule consists of a large number of monosaccharide molecules which are joined to one another by glycosidic linkage. The term polysaccharide is also intended to embrace an oligosaccharide. The polysaccharide can be homopolysaccharides or heteropolysaccharides. Whereas the homopolysaccharides contain only one kind of unit, the heteropolysaccharides consist of monomer units of different kinds.

The term "antisense oligonucleotide" refers to single stranded DNA or RNA that is complementary to a chosen sequence. In the case of antisense RNA, they prevent protein translation of messenger RNA strands by binding to them. Antisense DNA can be used to target a specific, complementary (coding or non-coding) RNA. If binding takes places this DNA/RNA hybrid can be degraded by the enzyme RNase H. Antisense oligonucleotides are generally from to 30, from 15 to 35, or from 18 to 25 nucleotides in length.

The term "shRNA" as used herein refers to short hairpin RNA which functions as RNAi and/or siRNA species but differs in that shRNA species are double stranded hairpin-like structure for increased stability. The term "RNAi" as used herein refers to interfering RNA, or RNA interference molecules are nucleic acid molecules or analogues thereof for example RNA-based molecules that inhibit gene expression. RNAi refers to a means of selective post-transcriptional gene silencing. RNAi can result in the destruction of specific mRNA, or prevents the processing or translation of RNA, such as mRNA.

As used herein, the term "aptamer" means a single-stranded, partially single-stranded, partially double-stranded or double-stranded nucleotide sequence capable of specifically recognizing a selected non-oligonucleotide molecule or group of molecules. Accordingly, aptamers are nucleic acid or peptide molecules that bind to a particular molecule of interest with high affinity and specificity (Tuerk and Gold, Science 249:505 (1990); Ellington and Szostak, Nature 346:818 (1990)). DNA or RNA aptamers have been successfully produced which bind many different entities from large proteins to small organic molecules. See Eaton, Curr. Opin. Chem. Biol. 1:10-16 (1997), Famulok, Curr. Opin. Struct. Biol. 9:324-9 (1999), and Hermann and Patel, Science 287:820-5 (2000). Aptamers can be RNA or DNA based. Methods for selecting aptamers for binding to a molecule are widely known in the art and easily accessible to one of ordinary skill in the art. Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. The aptamer can be prepared by any known method, including synthetic, recombinant, and purification methods, and can be used alone or in combination with other aptamers specific for the same target. Further, as described more fully herein, the term "aptamer" specifically includes "secondary aptamers" containing a consensus sequence derived from comparing two or more known aptamers to a given target. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and non-nucleotide residues, groups or bridges. In some embodiments, the aptamer recognizes the non-oligonucleotide molecule or group of molecules by a mechanism other than Watson-Crick base pairing or triplex formation.

As used herein, the term "ribozyme" means a single-stranded, partially single-stranded, partially double-stranded or double-stranded nucleotide sequence having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). At least six basic varieties of naturally-occurring enzymatic RNAs are known presently. In general, enzymatic nucleic acids act by first binding to a target RNA. Such binding occurs through the target-binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Methods of producing a ribozyme targeted to any target sequence are known in the art. Ribozymes can be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein.

Because transcription factors recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to up-regulate genes that are suppressed by the binding of a transcription factor. Examples of the utilization of decoy oligonucleotides can be found in Mann et al., J. Clin. Invest., 2000, 106: 1071-1075, which is expressly incorporated by reference herein, in its entirety.

As used herein, the term "calcimimetic compound" refers to a compound that binds to calcium sensing receptors and induces a conformational change that reduces the threshold for calcium sensing receptors activation by the endogenous ligand $Ca^{2+}$, thereby reducing parathyroid hormone (PTH) secretion. These calcimimetic compounds can also be considered allosteric modulators of the calcium receptors.

Exemplary calcimimetic compounds include, but are not limited to, those disclosed in, for example, European Patent No. 933 354 and 1 235 797; International Publication Nos. WO 01/34562, WO 93/04373, WO 94/18959, WO 95/11221, WO 96/12697, WO 97/41090; U.S. Pat. Nos. 5,688,938, 5,763,569, 5,962,314, 5,981,599, 6,001,884, 6,011,068, 6,031,003, 6,172,091, 6,211,244, 6,313,146, 6,342,532, 6,362,231, 6,432,656, 6,710,088, 6,908,935 and U.S. Patent Application Publication No. 2002/0107406, content of all of which is incorporated herein by reference in its entirety.

The disclosure is further illustrated by the following examples which should not be construed as limiting. The examples are illustrative only, and are not intended to limit, in any manner, any of the aspects described herein. The following examples do not in any way limit the invention.

EXAMPLES

In previous work by the inventors, they showed that early calcification of atherosclerotic plaques associates with macrophage accumulation. Chronic renal disease (CRD) and mineral imbalance accelerates calcification and the subsequent release of matrix vesicles (MV)—precursors of microcalcification. In the present study, the inventors discovered that macrophage-derived MV contribute directly to microcalcification.

Materials and Methods

Human Tissue Samples:

Discarded human carotid endarectomy specimens (n=136 patients) were collected in accordance with a protocol approved by the Institutional Review Board of Brigham and Women's Hospital. Tissue samples were analyzed by immunohistochemistry and transmission electron microscopy. Human carotid endarectomy samples were collected and embedded in OCT compound. Cryosections of 6-μm thickness were stained for macrophages (CD68; Dako, Carpinteria, Calif., USA) and smooth muscle cells (SMC; α-smooth muscle actin [α-SMA; Dako, Carpinteria, Calif., USA]).

Mice:

Wild-type (WT) mice and $apoE^{-/-}$ mice in C57BL/6 background were purchased from the Jackson Laboratory (Bar Harbor, Me., USA). $S100A9^{-/-}$ ($MRP-14^{-/-}$) mice in C57BL/6 background were provided by Dr. Nancy Hogg. $S100A9^{-/-}$ mice were crossbred with apolipoprotein E-deficient ($ApoE^{-/-}$) mice in a C57BL/6 background (Jackson Laboratory, Bar Harbor, Me., USA) to generate compound mutant double-deficient mice ($S100A9^{-/-}ApoE^{-/-}$), see Croce et al., Circulation, 2009, 120: 427-436. Single mutant $ApoE^{-/-}$ mice were used as controls. All mice had a congenic C57BL/6 background and were maintained in animal facilities at Harvard Medical School. A subset of WT mice (n=8) were fed a high-fat diet (HFD). CRD was induced in $apoE^{-/-}$ mice by 5/6 nephrectomy, as previously described in Aikawa et al., Circulation, 2009, 119:1785-94. Animal care and procedures were approved by the Institutional Animal Care and Use Committees, and were performed in accordance with the guidelines of the American Association for Accreditation of Laboratory Animal Care and the National Institutes of Health.

Immunohistochemistry/Immunofluorescence:

Immunohistochemistry was performed on fresh frozen sections of mouse aortic arches and human carotid endarterectomy specimens, as previously described in Aikawa et al., Circulation, 2009, 119:1785-94. Briefly, tissue samples were frozen in OCT compound (Sakura Finetech, Torrance, Calif., USA) and 6-µm serial sections were cut. Antibodies included annexin V (1:100; Abcam, Cambridge, Mass., USA), S100A9 (1:100; R&D Systems, Mineapolis, Minn., USA), CD68 (1:70; Dako, Carpinteria, Calif., USA), and αSMA (1:100; Dako, Carpinteria, Calif., USA). Immunohistochemistry used the avidin-biotin peroxidase method. The reaction was visualized with 3-amino-9-athyl-carbazol substrate (AEC; Sigma Chemical, St. Louis, Mo., USA). Adjacent sections treated with PBS in place of a primary antibody were used as negative controls. Images were captured with a digital camera (Nikon DXM 1200F, Nikon Inc., Melville, N.Y., USA). Fluorescence visualized S100A9 and annexin V labeled with Alexa Fluor® 488/594. Images were captured and processed with the epifluorescence microscope (Eclipse 80i, Nikon Instruments Inc., Melville, N.Y., USA) with a cooled CCD camera (Cascade, Photometrics, Tucson, Ariz., USA).

Detection and Quantification of Mineralization:

Bisphosphonate-conjugated imaging agent that binds to hydroxyapatite (OsteoSense680, VisEn Medical Inc., Woburn, Mass., USA), elaborating fluorescence evident through the near-infrared window (ex/em 650/680 nm), detected mineralization, as previously described in Aikawa et al., Circulation, 2007, 116:2841-2850 and Aikawa et al., Circulation, 2007, 115:377-386. Frozen sections of human carotid endarterectomy specimens were treated with OsteoSense680 for a minimum of 2 hours before imaging. ApoE$^{-/-}$ mice were intravenously injected with the NIRF imaging agent and tissue was harvested after 24 hours. Frozen sections of the aortic arch were imaged ex vivo. Images were captured and processed with the epifluorescence microscope (Eclipse 80i, Nikon Instruments Inc., Melville, N.Y., USA) with a cooled CCD camera (Cascade, Photometrics, Tucson, Ariz., USA). In order to quantify the calcifying vesicular structures, MV, we utilized an imaging analyzing technique developed in our laboratory (KY). Prior to making a binary image of Osteosense-labeled macrophage-rich plaques, the image was processed utilizing edge filter for good selection of MV from the images. We counted the number of calcifying vesicular structures in an average of 3 high power fields (×400 magnification) in 8 patients. A range threshold was obtained by calculating the cumulative frequency and vesicular structures with pixel number ranging from 40 to 115 were counted as calcifying vesicles. Osteosense-labeled vesicular structures below 40 pixels were removed as background, and vesicles measured above 115 were removed as micro/macrocalcifications.

Transmission Electron Microscopy (TEM) Analysis of MV in Calcified Arteries:

Tissue was immersion fixed in 2.5% glutaraldehyde, 2% paraformaldehyde, in 0.1M cacodylate buffer pH 7.4 (modified Karnovsky's fixative) and post-fixed in 1% osmium tetroxide, dehydrated and embedded in Epon resin. Thin sections (80-nm thickness) were placed on carbon coated and glow discharged formvar coated copper slot grids; these were contrast stained with 2% uranyl acetate and lead citrate. Grids were imaged on a JEOL 1400 TEM equipped with a side mount Gatan Orius SC1000 digital camera.

Immuno-EM on Calcified Arteries:

Tissues were immersion fixed in 2.5% glutaraldehyde, 2% paraformaldehyde, in 0.1M Cacodylate buffer pH 7.4 (modified Karnovsky's fixative). The tissues were dehydrated and embedded in acrylic resin. Thin sections (80-nm thickness) were placed on carbon coated and glow discharged formvar coated nickel slot grids. Blocked grids were incubated in primary antibody at RT for 1 hour, followed by an appropriate gold-conjugated secondary antibody for 1 hour at RT. After fixing with 1% glutaraldehyde in TBS, sections were contrast stained with uranyl acetate. Grids were imaged on a JEOL 1400 TEM equipped with a side mount Gatan Orius SC1000 digital camera. Primary antibodies included rabbit anti-human annexin V (1:200; Abcam, Cambridge, Mass., USA), mouse anti-human S100A9 (1:200; R&D Systems, Mineapolis, Minn., USA), and CD68 (1:100; Dako, Carpinteria, Calif., USA). Secondary antibodies included goat anti-rabbit 10-nm colloidal and gold anti-mouse 10-nm colloidal gold (1:25; Abcam, Cambridge, Mass., USA).

Culture and Stimulation of Murine Macrophages:

Murine macrophage-like cells, RAW 264.7, were seeded at a density of $1.6 \times 10^5$ cells per cm$^2$. Prior to experiment, the cells were serum starved in DMEM containing 0.1% FCS. After 24 hours, either control media (DMEM containing 0.1% FCS) or calcifying media (DMEM containing 0.1% FCS, supplemented with stimuli as indicated). Stimuli included Ca/P (3 mmol/L calcium/2 mmol/L phosphate), P (2 mmol/L phosphate), 20 ng/ml TNFα (PeproTech, Rocky Hill, N.J., USA), Ca/P+TNFα (3 mmol/L calcium/2 mmol/L phosphate and 20 ng/ml TNFα), S100A9 (50 ng/ml recombinant mouse S100A9 (Novus Biologicals, Littleton, Colo., USA)). CaCl$_2$ and NaH$_2$PO$_4$ (Sigma-Aldrich Corp., St. Louis, Mo., USA) were added to supplement calcium and phosphate in the media.

Time Lapse Imaging of Macrophages:

Macrophages, seeded onto glass-bottomed dishes, were serum starved as previously described. After 24 hours the cells were loaded with 5 mmol/L Fluo-3 (Life Technologies, Grand Island, N.Y., USA). Calcium influx was visualized by imaging cells before and after stimulation with Ca/P in Tyrode solution. In the same vein, the release of vesicles was visualized after Ca/P-stimulation by time lapse microscopy. In both protocols the following were used: a 60× oil immersion objective, the Eclipse 80i microscope (488 nm, Nikon, Melville, VY) and the NIS element software (Nikon, Melville, VY). For the visualization of MV release, images were taken every 10 seconds over 24 hours.

Visualization of Phosphatidylserine (PS) Externalization:

Murine macrophage-like cells, RAW 264.7, were seeded onto glass-bottomed dishes and serum starved as previously described. After 24 hours, the media was exchanged for control media and 20 µl/ml pSIVA-IANBD (Abeam, Cambridge, Mass., USA) added directly to cell culture before stimulation. pSIVA™ is an Annexin XII-based polarity sensitive probe with a high affinity for PS that binds reversibly to the cell membrane, enabling the detection of irreversible as well as transient PS exposure. pSIVA™ is conjugated to IANBD, which fluoresces only when pSIVA is bound to the cell membrane thus allowing for the detection of PS exposure. The cells were visualized before and after Ca/P-stimulation using a 60× oil immersion objective, the Eclipse 80i microscope (488 nm, Nikon, Melville, VY) and the NIS element software (Nikon, Melville, VY).

Isolation of Peritoneal Macrophages from Mice:

Peritoneal macrophages were elicited by injecting 1.5 ml 4% aged thioglycolate into the peritoneal cavity. After 4 days, the peritoneal macrophages were harvested by injecting RPMI 1640 medium into the peritoneal cavity, gently massaging the abdominal area, and removing the liquid containing the resident macrophages. After washing with PBS, the cells were seeded at a density of $1-2 \times 10^6$ cells per well in serum-free medium. After 2 hours, the cells were washed with PBS to remove non-adherent cells, and the adherent cells were incubated with RPMI 1640 containing 10% fetal bovine serum for 48 hours. Due to the high phosphate concentration already present in RPMI-1640, the cells were switched to α-MEM prior to stimulation. Peritoneal macrophages were serum starved in α-MEM containing 0.1% fetal bovine serum for 24 hours before addition of either control media (α-MEM containing 0.1% fetal bovine serum) or calcification media (α-MEM containing 0.1% fetal bovine serum, supplemented with 3 mmol/L calcium chloride/2 mmol/L sodium phosphate) for an additional 24 hours prior to analysis.

Isolation and Culture of Human Macrophages:

Human peripheral blood mononuclear cells were isolated by density gradient centrifugation, as described previously in Aikawa et al. (*Circulation,* 2001, 103:276-283) and were cultured in IMDM that contained 5% human serum for 7 days. After 7 days, the cells morphologically appeared to have differentiated into macrophages, and the cells were then cultured in DMEM. After 10 days, some differentiated macrophages were either transfected with siRNA or serum starved in DMEM containing 1% human serum for 24 hours, before addition of control media (DMEM containing 1% human serum) or calcification media (DMEM containing 1% human serum, supplemented with 3 mmol/L calcium chloride/2 mmol/L sodium phosphate) for an additional 24 hours prior to analysis.

Short Interfering (siRNA) Transfection of Human Macrophages:

Short interfering RNA oligonucleotides predesigned by Dharmacon Thermo Scientific included ON-TARGETplus Non-targeting Pool, Human S100A9 ON-TARGETplus SMARTpool, and Human ANXA5 ON-TARGETplus SMARTpool. Transfection of human macrophages was performed using Dharmafect 4 transfection reagent (Thermo Scientific, Lafayette, Colo., USA), according to the manufacturer's protocol. Briefly, 100 nM siRNA was diluted in OPTIMEM, mixed with Dharmafect 4, and incubated for 20 minutes at room temperature. This mixture was added drop-wise onto human macrophages, which were then incubated in DMEM supplemented with 5% human serum. After 48 hours, the cells were serum starved in DMEM containing 1% human serum and antibiotics for 24 hours. The cells were then incubated in control media (DMEM containing 1% human serum and antibiotics) or in calcifying media (DMEM containing 1% human serum and antibiotics and supplemented with 3 mmol/L calcium chloride/2 mmol/L sodium phosphate) for 24 hours. MV were analyzed using the calcium or ALP assay (BioVision, Inc., Milpatas, Calif., USA), or lysed for analysis by Western blot and the cells were lysed using Trizol and analyzed by RT-PCR to determine efficiency of the knockdown.

Analysis of Cell Viability and Apoptosis:

Cell viability, assessed by measuring live-cell protease activity, and apoptosis, assessed via detection of Caspase 3/7 activation, was analyzed using ApoLive-Glo Multiplex assay (Promega, Madison, Wis., USA), according to the manufacturer's instructions.

Reverse Transcription and Quantitative Polymerase Chain Reaction:

Total RNA was isolated from cell isolates and reverse transcribed using an Applied Biosystems 2720 thermal cycler (Applied Biosystems, Foster City, Calif.). TaqMan quantitative polymerase chain reaction (PCR) detection of human S100A9 and annexin V, and of mouse inducible nitric oxide synthase (iNOS), mannose receptor 1 (MRC-1), IL6, and IL1β, was performed on an ABI PRISM 7900HT sequence detection system (Applied Biosystems, Foster City, Calif., USA). Quantitative PCR values were normalized to β-actin. Relative fold changes in value were calculated by the comparative threshold cycles ($C_t$) method, $2^{-\Delta\Delta C_T}$.

Isolation of Macrophage-Derived MV:

Cell media were collected after approximately 24 hours and subjected to centrifugation at 1000 g for 5 minutes to remove cell debris, followed by 16500 g for 5 minutes to remove apoptotic bodies and any larger vesicles. MV fraction was harvested from the media by ultracentrifugation at 100000 g for 40 minutes at 4° C. (Optima Max Ultracentrifuge, Beckman Coulter, Inc., Indianapolis, Ind., USA).

Calcium Content Analysis:

MV were analyzed using the calcium colorimetric assay (BioVision, Inc., Milpatas, Calif., USA), according to the manufacturer's specifications.

Alkaline Phosphatase (ALP) Activity:

MV were analyzed using the ALP assay (BioVision, Inc., Milpatas, Calif., USA), according to the manufacturer's specifications.

Protein Concentration:

Protein concentration was determined by the Pierce BCA assay (Thermo Scientific, Rockford, Ill., USA), according to the manufacturer's specifications.

Negative Staining of Isolated MV from RAW 264.7 Cells:

Nickel grids with 200 mesh, formvar, carbon coating, and freshly glow discharged were used for the negative staining of MV. Each grid was placed on a 20-μl droplet of sample (approximately 1 mg/ml in PBS) for 5 minutes. After washing with water, grids were negatively stained with phosphotungstic acid. Grids were imaged on a JEOL 1400 TEM equipped with a side mount Gatan Orius SC1000 digital camera.

Quantification of MV in Mouse Plasma:

Flow cytometry was used to detect MV in mouse plasma from WT, apoE$^{-/-}$, and apoE$^{-/-}$ S100A9$^{-/-}$ mice (Tzur et al., PLoS One. 2011), fed a HFD. Mouse blood was separated into plasma by 1500 g centrifugation for 15 minutes. A platelet poor fraction was obtained by spinning the plasma for an additional 2 minutes at 13000 g. The MV flow cytometry protocol combined 20 μL of mouse platelet poor plasma, 42.5 μL of filtered (0.22 μm) annexin V binding buffer (1× Tris Buffered Saline with 2.5 mM CaCl$_2$), and 2.5 μL of Annexin V-FITC (10 μg/mL, Bender MedSystems (eBioscience), San Diego, Calif., USA) to enable quantification of phosphatidylserine-positive MVs. Prior to flow cytometry, annexin V-labeled MVs were combined with 385 μL of annexin V binding buffer and 50 μL of fluorescent counting beads, which enabled determination of flow rate and MV concentration (Flow-Count Fluorospheres, Beckman Coulter, Brea, Calif., USA). Sample analysis was performed on a FACS Calibur flow cytometer (Becton Dickinson, Franklin Lakes, N.J., USA), and we analyzed the flow cytometry data with FCS Express software 3.0 (DeNovo Software, Los Angeles, Calif., USA). MV were identified by side scatter size compared to sizing beads (Megamix, Biocytex 7801, France), and by annexin V binding as described previously. We defined the MV gate as annexin V-positive events sized <1 μm. Annexin V binding to phosphatidylserine-containing plasma membranes is calcium dependent; thus, samples treated with the calcium-chelating agent ethylenediaminetetraacetic acid (EDTA, 20 mM) served as a negative control for annexin V gating. The threshold of annexin V-positive MV events was set above the 99.99th percentile of the EDTA-treated negative control sample. The FACS analysis of the mouse plasma samples were made using randomly numbered tags without knowledge of which group they belonged, in a blinded fashion. The groups were identified only when performing the final data analysis.

Aggregation Potential of MV:

MV size was measured using a time-resolved particle analyzer (EX-300, Kowa Company, Ltd., Nagoya, Japan). Some remodeling was performed to improve the sensitivity against small particle, including equipping the device with preamps and analog/digital converter. According to a fitting curve (size versus scattering light intensity) obtained from measurements of size-standard nano particles (Nanosphere with 20, 60, 150 and 500 nm in diameter; Thermo Scientific, Fremont, Calif., USA) and refractive indeces (RI) of Nanosphere (RI=1.59) and MV (using the previously reported (Neto et al., Biophys J., 2006, 91:1108-1115) RI of macrophages; RI=1.38±0.02), we calculated actual sizes of MV. Aggregation potential of MV was evaluated by measuring their size growth under continuous stirring of the media (control or Ca/P-stimulation) for 10 min.

Western Blotting:

Cell or MV samples were lysed in RIPA buffer containing protease inhibitor cocktail (Roche, Indianapolis, Ind., USA). The lysates were centrifuged at 13000 g for 10 minutes. Supernatants were collected, and the protein concentration was determined using the BCA assay (Thermo Scientific, Rockford, Ill., USA). For Western Blotting, 10-20 µg of protein lysate were separated on 15% SDS-PAGE and transferred to a PVDF membrane using the iBlot dry transfer system (Life Sciences, Grand Island, N.Y., USA). The membrane was blocked for non-specific binding in blocking buffer (TBS-T ([Tris-buffered saline with 0.05% Tween-20] containing 3% dry milk), and incubated with primary antibody. Antibodies for detection included annexin V (1:250) S100A9 (1:1000), CD9 (1:500; All Abcam, Cambridge, Mass., USA), and TSG101 (1:500; GeneTex Inc., Irvine, Calif., USA). Following incubation with primary antibodies, and washing wells with TBS-T, membranes were incubated with horseradish peroxidase-conjugated secondary antibody (1:5000, Amersham Biosciences, Piscataway, N.J., USA) and visualized using the ECL system (PerkinElmer, Billerica, Mass., USA). β-actin (1:5000; Novus Biologicals, Littleton, Colo., USA) was used as a loading control to demonstrate equal sample loading. Membranes were imaged using the ImageQuant™ LAS 4000 (GE Healthcare, Piscataway, N.J., USA) and image band intensity was measured using ImageJ 1.45 software.

Statistical Analysis:

Data were analyzed by t-test or 1-way ANOVA with Bonferroni post hoc test using PRISM software (GraphPad, San Diego, Calif.). Data show mean±SD. $P<0.05$ was considered statistically significant. The n values represent the number of patients or donors studied, or the number of times the experiment was performed (the latter refers to experiments using RAW267.4, the macrophage-like cell line).

Results and Discussion

MV Released from Macrophages Contribute to Intimal Microcalcification.

Figure 5:
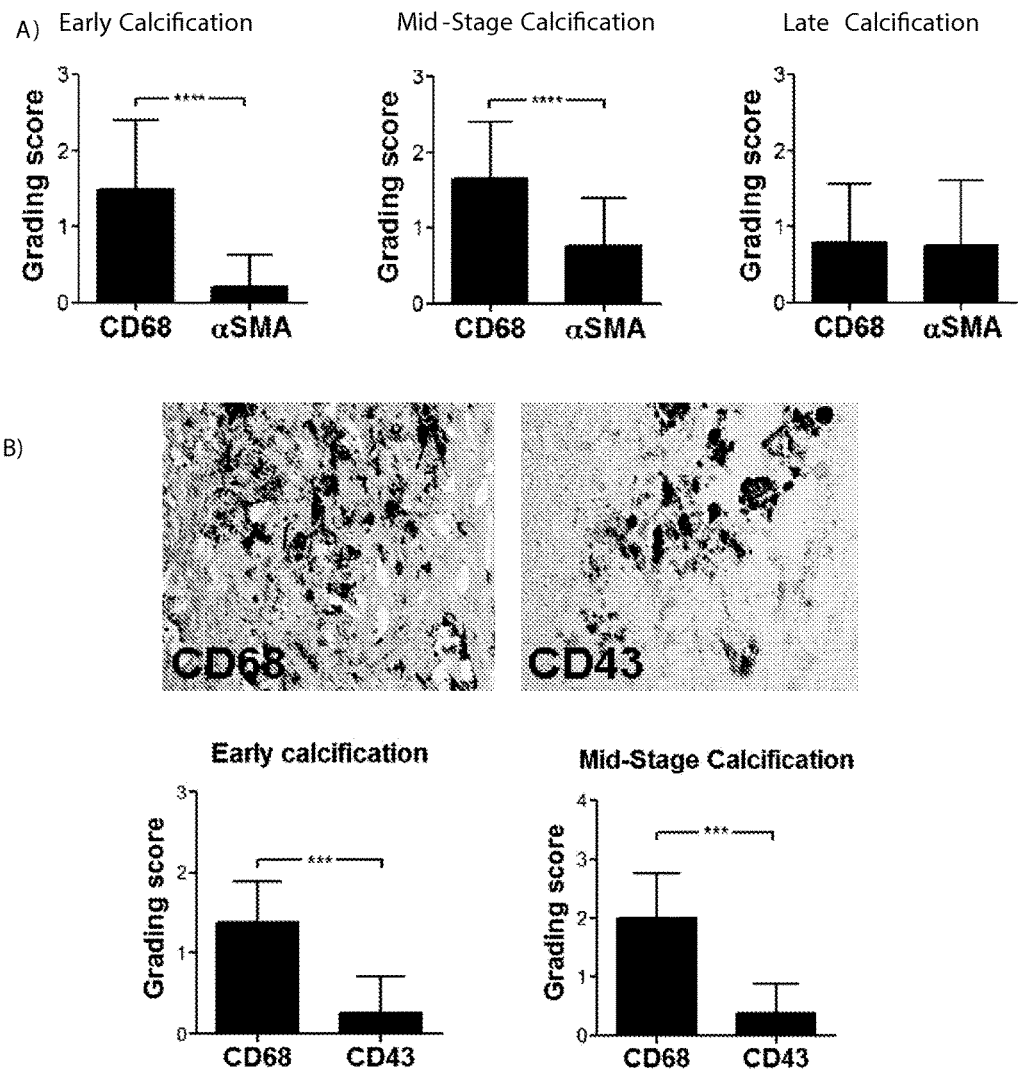
FIG. 5A shows that macrophages associate with MV-rich areas in human calcified atherosclerotic plaques (****p<0.0001). Regions of early calcification were vesicle-rich calcified areas (calcification <100 μm in size; 87 sections from 75 patients); mid-stage calcification areas were vesicle-rich with larger calcified areas (101 sections from 89 patients), and regions of late calcification were large calcified areas, with no evidence of vesicles (20 sections from 19 patients). Co-localization of CD68-positive macrophages and vesicular structures was identified in both regions of early and mid-stage calcification (161 sections from 127 patients). The number of sections analyzed overall was 176 from 136 patients. Grading 0=<25% weak expression; 1=>25% strong expression or <50% weak expression; 2=≥50% strong expression or <75% weak expression; 3=>75% expression.
FIG. 5B shows that a lack of neutrophils was apparent in regions of both early (n=8; *p<0.001) and mid-stage calcification (n=8; *p<0.0001) of human atherosclerotic plaques.
Figure 6:
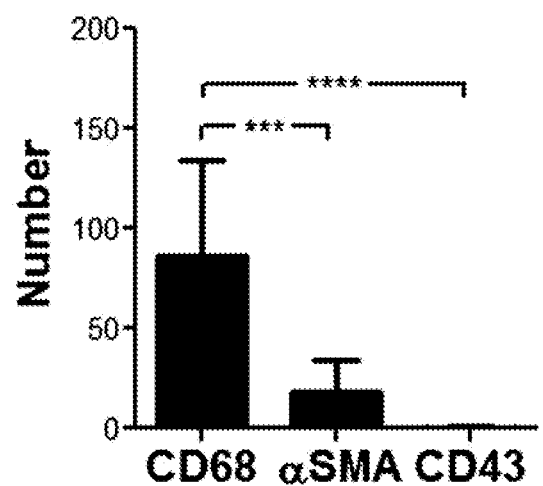
FIG. 6 shows that a larger number of macrophages (CD68-positive cells) are apparent in MV-rich areas in human calcified atherosclerotic plaques (n=8, *p<0.001, **p<0.0001), demonstrating the frequency of macrophages releasing MV in the plaque compared to smooth muscle a-SMA positive cells and neutrophils (CD43-positive cells).
Figure 7:
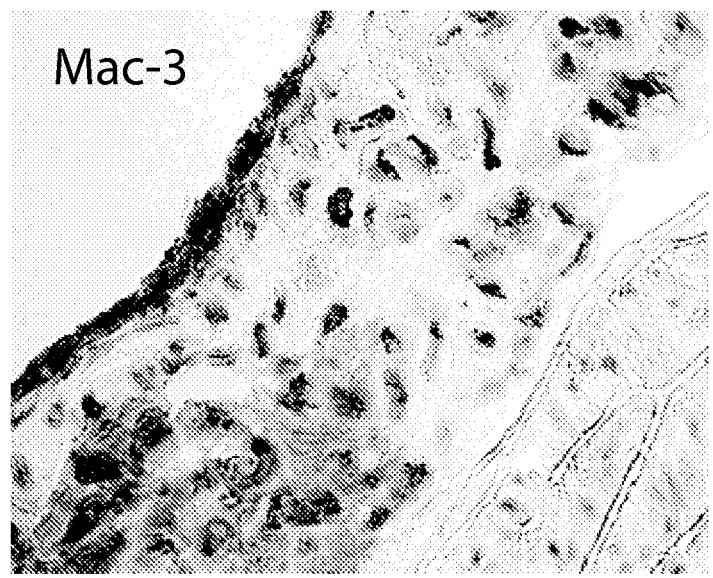
FIG. 7 shows that Mac3-positive cells (red reaction product) were evident in and adjacent to the region of calcification (hematoxylin; blue) in atherosclerotic plaques of apoE$^{-/-}$ mice with 5/6-nephrectomy.
Figure 8:
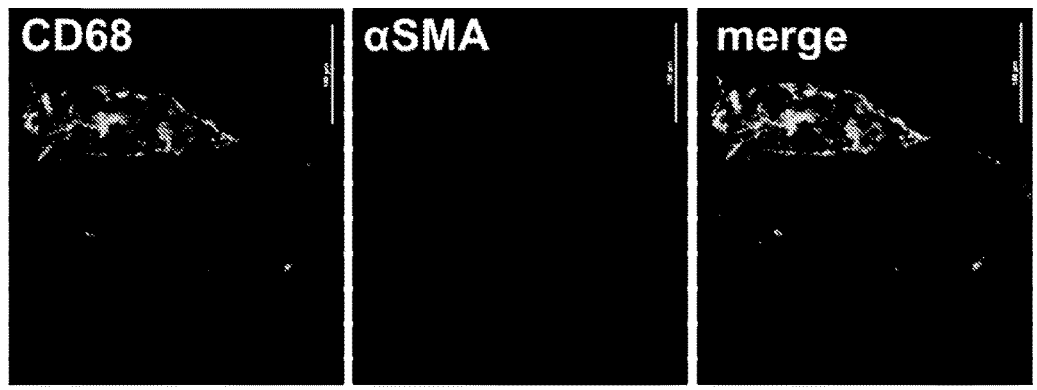
FIG. 8 shows little to nil colocalization of CD68-positive and αSMA-positive areas in calcified plaques from CRD apoE−/− mice.

Immunohistochemical analysis of macrophages (CD68) and SMC (α-smooth muscle actin; α-SMA) in 136 human carotid endarterectomy samples demonstrated that abundant macrophages associate with regions of MV (FIG. 1A), to a greater extent than α-SMA-positive or CD43-positive cells in areas of spotty calcification, a characteristic associated with biomechanical instability (FIG. 1B and FIGS. 5 and 6 for quantitative analysis). Ex vivo near-infrared fluorescence (NIRF) imaging of hydroxyapatite-binding nanoparticles visualized numerous calcifying MV within calcified atherosclerotic plaques from humans ($2784\pm1073$ MV/mm$^2$; n=8; FIG. 1C) and from apoE$^{-/-}$ mice (FIG. 1D) with CRD, induced by 5/6 nephrectomy (Goodman et al., Am J Kidney Dis., 2004, 43:572-9). We used transmission electron microscopy (TEM) to characterize MV within plaques. Immunogold labeling visualized release of CD68-positive MV from macrophages (FIG. 1E). MV abound in human and mouse plaques, and associate with cholesterol crystals (FIGS. 1F and 1G). Plaque areas rich in MV showed microcalcification and dense hydroxyapatite crystals localized on the membranes of calcifying MV (FIG. 1I1).

Pro-Inflammatory Macrophages Release Microcalcification-Generating MV.

Figure 2B:
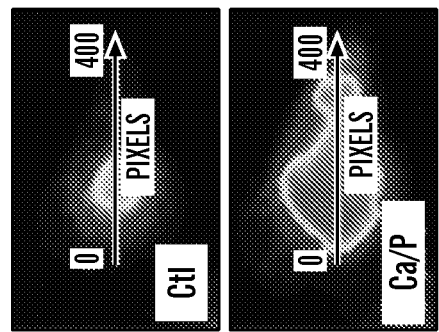
FIGS. 2A-2J show that macrophages release microcalcification-generating MV.
Figure 2A:
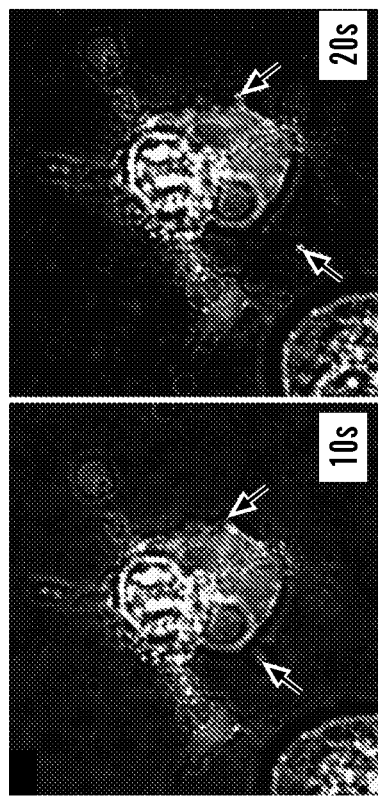
Figure 2E:
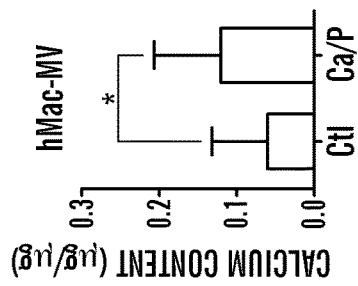
Figure 2D:
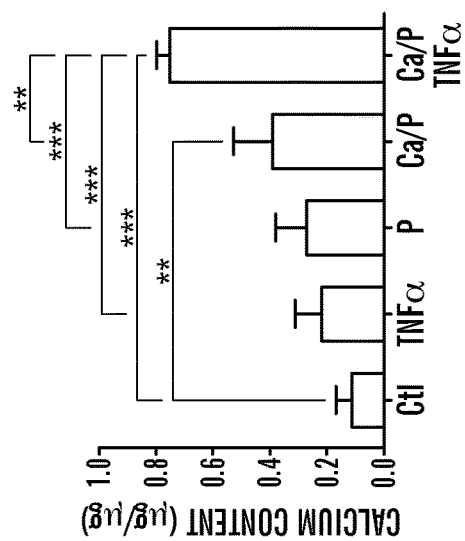
Figure 2C:
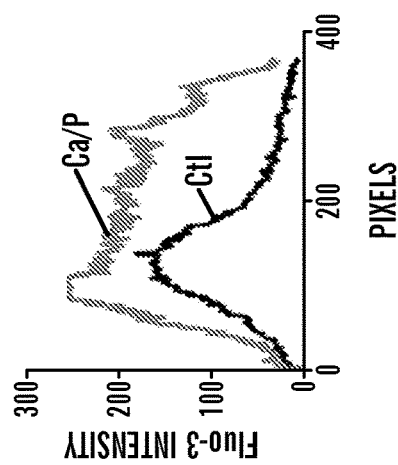
Figure 2H:
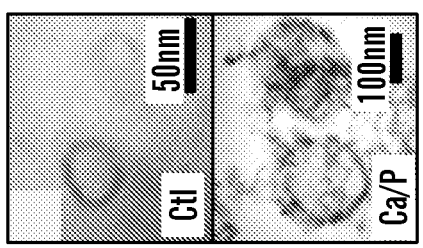
Figure 2G:
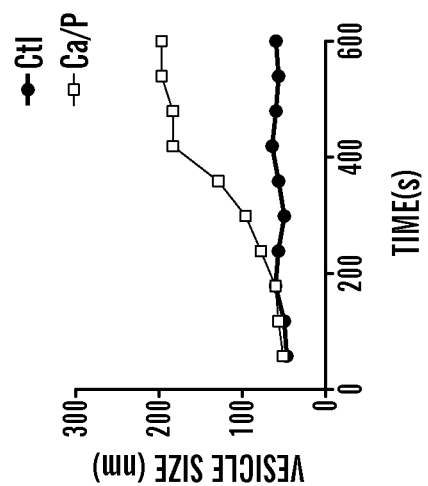
Figure 2F:
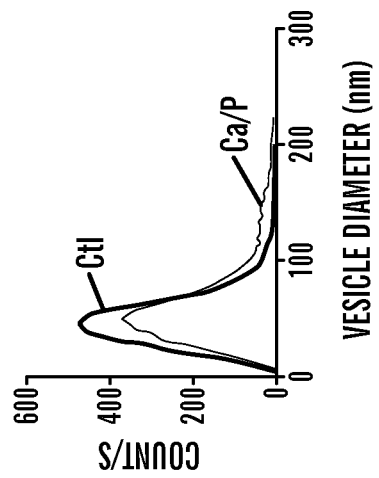
Figures 2I, 2J:
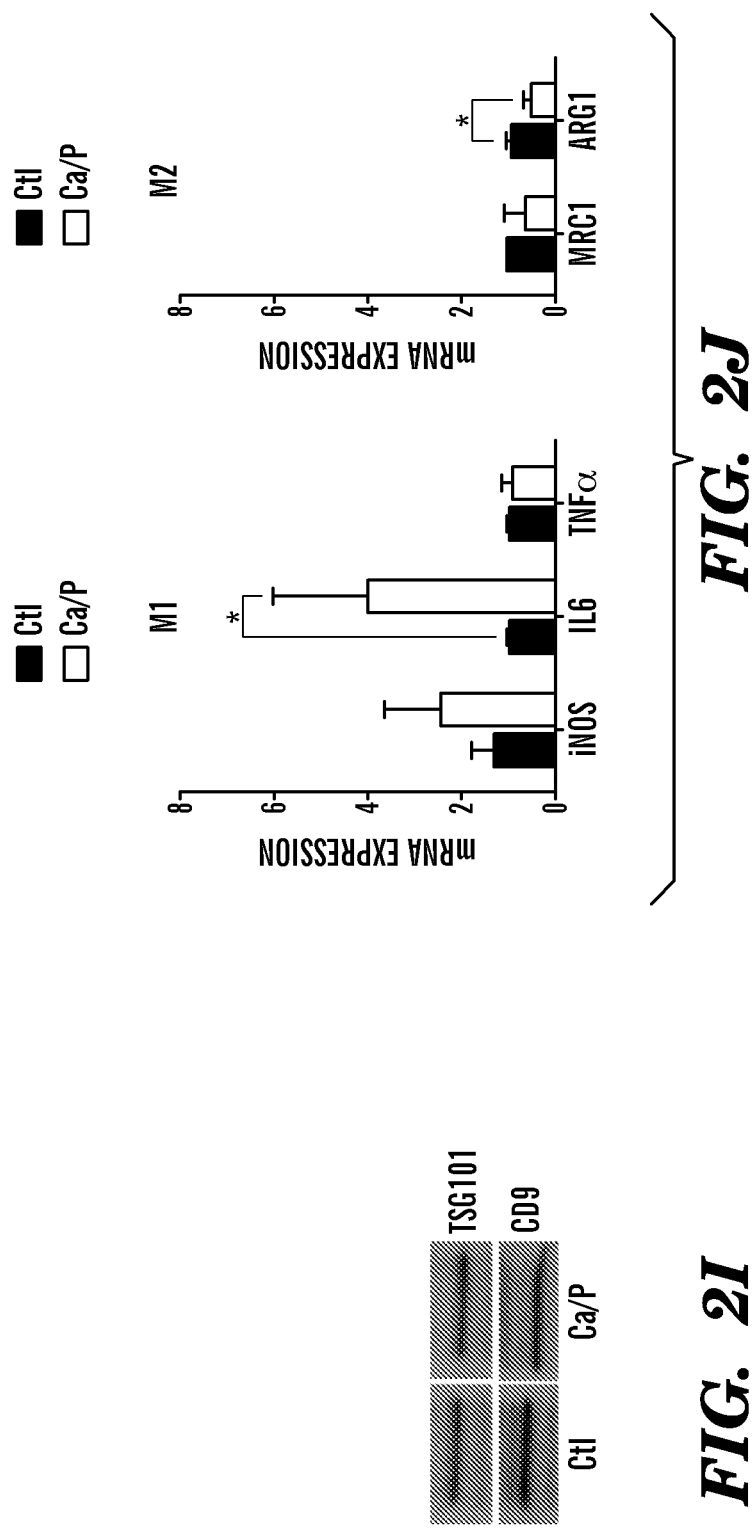
Figure 9:
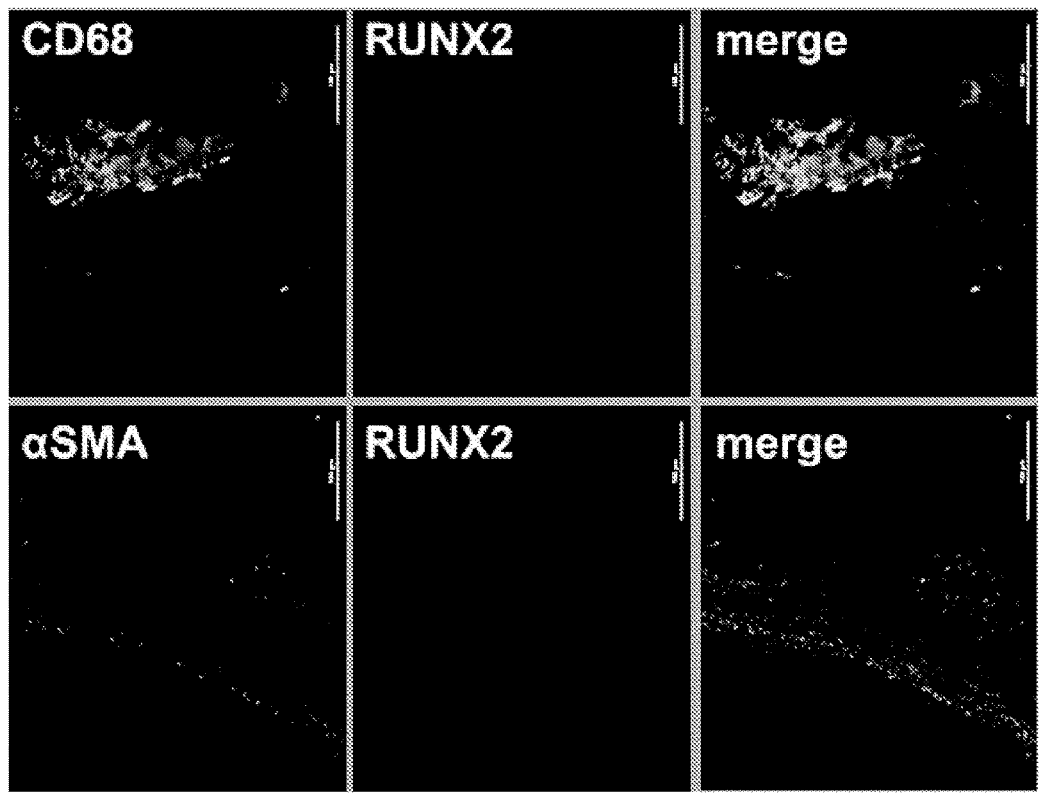
FIG. 9 shows that CD68-positive regions did not colocalize with areas of osteogenic activity, determined via the use of Runx2. However αSMA-positive cells were observed to colocalize with Runx2.
Figure 10:
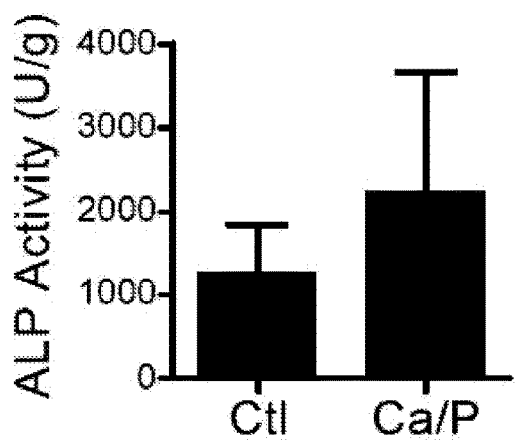
FIG. 10 shows that MV released from murine macrophage-like cells under calcifying conditions have higher ALP activity than MV released under non-calcifying conditions (n=5).

Time lapse imaging of macrophages loaded with Fluo-3, a calcium indicator, showed vesicle release from membranous protrusions (FIG. 2A) and calcium influx after stimulation with 3 mmol/L calcium/2 mmol/L phosphate (Ca/P; FIGS. 2B and 2C). Ca/P-stimulated macrophages released MV (Mac-MV) capable of mineralization, with increased calcium content (FIGS. 2D and 2E), alkaline phosphatase (ALP) activity (FIG. 9), and suggested aggregation potential (FIGS. 2F and 2G). TEM of MV released by control macrophages in vitro identified membrane-bound vesicles 30-300 nm, showing hydroxyapatite nucleation on the membrane and inside the vesicles after Ca/P stimulation (FIG. 2H). Mac-MV possessed exosomal markers (FIG. 2I) and were smaller than those described for apoptotic bodies. Additionally, Ca/P stimulation did not affect the viability or apoptotic levels of mouse macrophages (FIG. 10). Mouse macrophages stimulated with Ca/P possessed higher gene expression of inducible nitric oxide synthase (iNOS) and interleukin-6 (IL-6) (FIG. 2J), markers in mice of a pro-inflammatory "M1" macrophage phenotype, while "M2" markers tended to decrease.

PS-S100A9-Annexin V Complex Facilitates MV Mineralization.

Figure 3A:
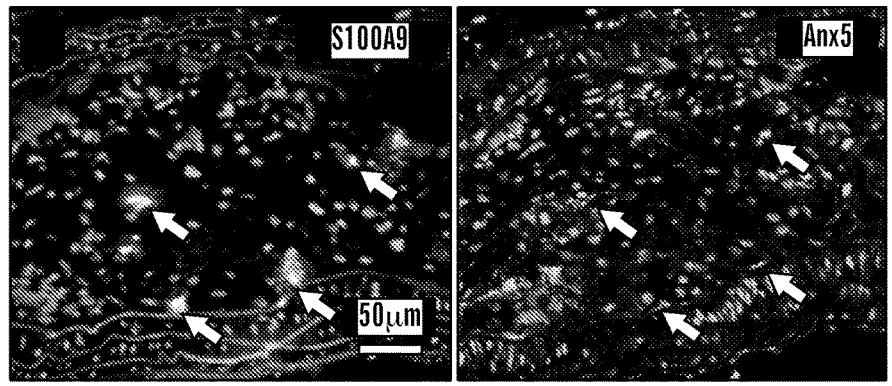
FIGS. 3A-3G show that PS-Anx5-S100A9 complex facilitates MV mineralization.
Figure 3B:
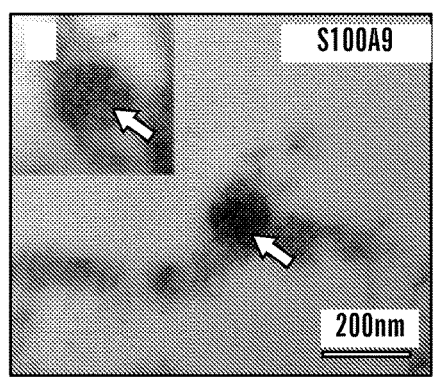
Figure 3C:
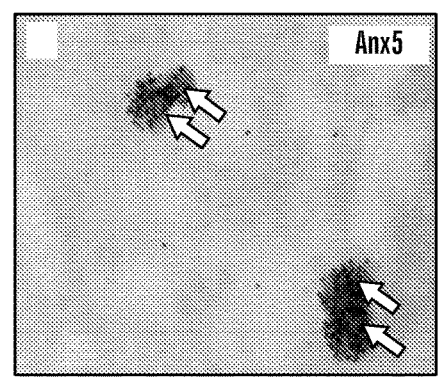
Figure 3D:
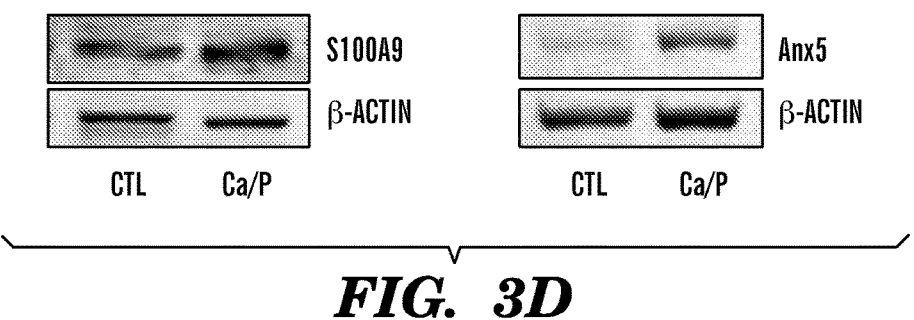
Figure 3E:
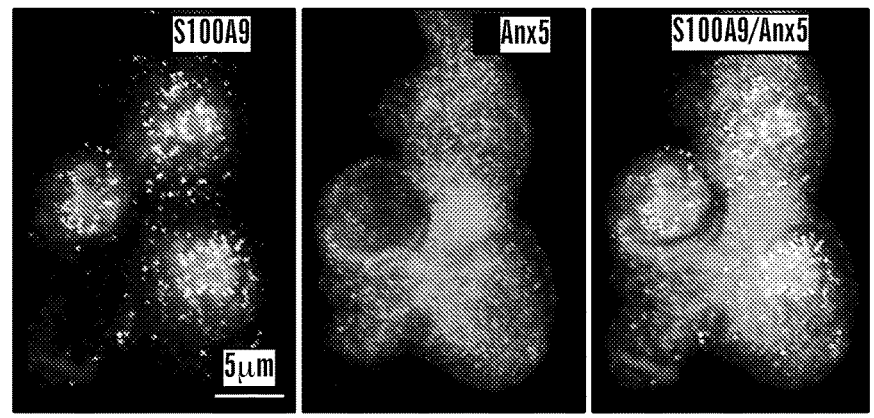
Figure 3F:
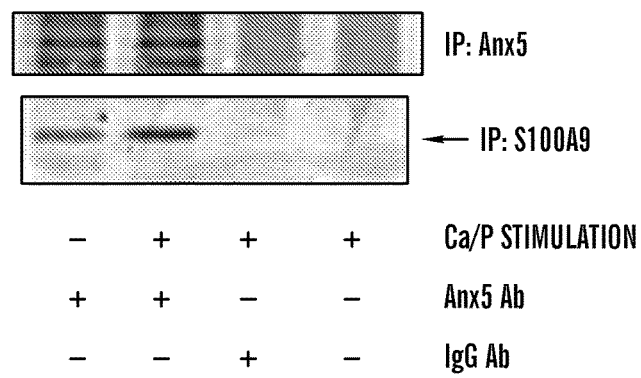
Figure 3G:
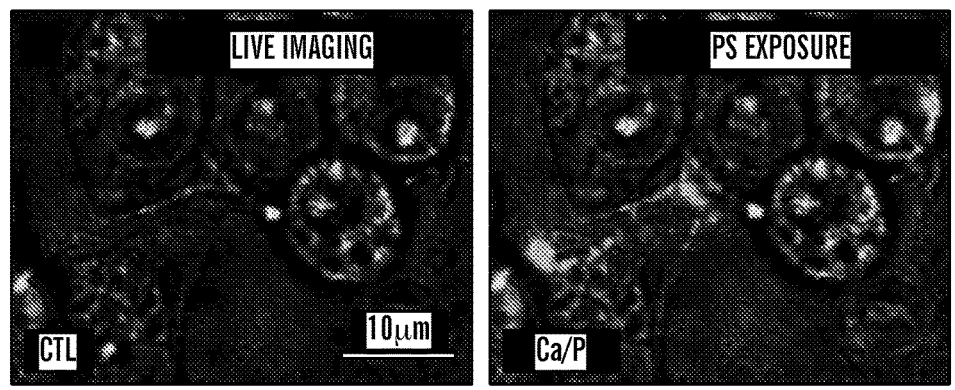
Figure 11:
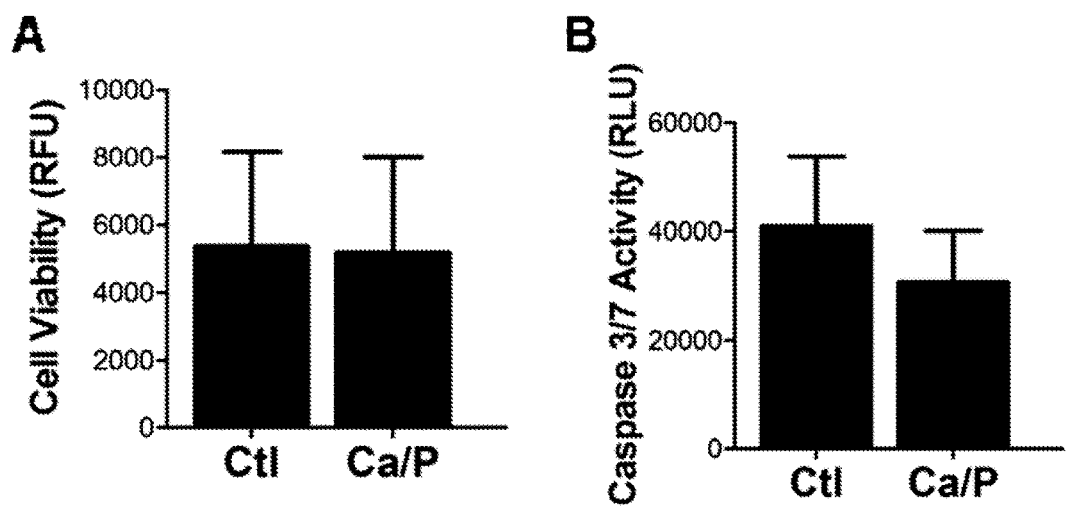
FIG. 11A shows that calcifying conditions used for in vitro experiments did not affect viability of the murine macrophage-like cells (n=4).
FIG. 11B shows analysis of caspase 3/7 activity in the same cells demonstrating that the calcifying conditions used for in vitro experiments did not induce apoptosis (n=4).
Figure 12:
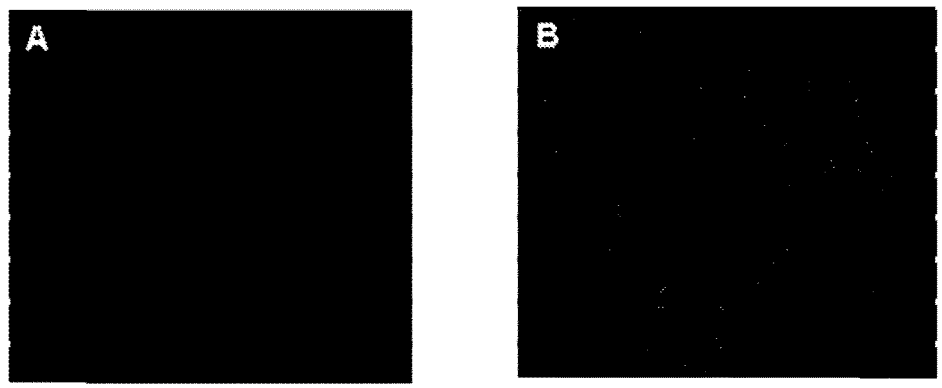
FIG. 12A shows the negative control for S100A9 immunofluorescence shown in FIG. 3A.
FIG. 12B shows the negative control for annexin V immunofluorescence shown in FIG. 3B.
Figure 13:
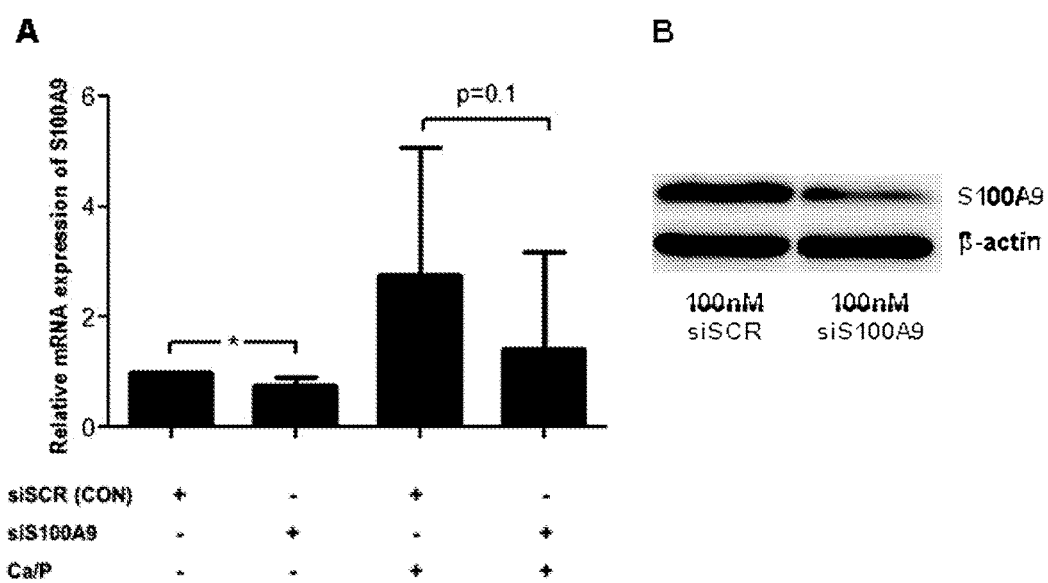
FIG. 13A shows gene expression of S100A9 after transfection of human macrophages with siRNA (n=4; *p=0.05).
FIG. 13B shows protein expression of S100A9 by Western blotting was knocked down (~70%) by siRNA in human macrophages in vitro.

Annexins contribute to SMC and osteoblast-derived MV-mediated calcification (Chen et al., *J Bone Miner Res.*, 2008, 23:1798-805; Kapustin et al., *Circ Res.*, 2011, 109:e1-12; and Kirsch et al., *J Bone Miner Res.*, 2003, 18:1872-81). S100A9/MRP-14-positive MV were identified in calcified plaques (McCormick et al., *J Biol Chem.*, 2005, 280:41521-9). Calcified plaques of CRD apoE$^{-/-}$ mice showed expression of both S100A9 and Anx5 (FIGS. 3A and 11). In addition, S100A9 and Anx5 co-localized with MV in calcified regions of human atheroma (immunogold TEM, FIGS. 3B and 3C). Ca/P-stimulation enriched S100A9 and Anx5 expression in mouse Mac-MV (FIG. 3D). We hypothesized that S100A9 and Anx5 form a complex in Mac-MV, similar to the complex formation of S100A9 and annexin VI (Bode et al., *J Biol Chem.*, 2008, 283:31776-84). The co-localization and co-immunoprecipitation analysis of S100A9 and Anx5 in cultured mouse macrophages supported this conjecture (FIGS. 3E and 3F). Ca/P-stimulation of mouse macrophages augmented the association between S100A9 and Anx5 (FIG. 3F). Anx5 and phosphatidylserine (PS) have proved critical for growth plate-MV mineral nucleation (Grskovic et al., J Bone Miner Res., 2012, online first), but whether nucleation occurs on the inside or outside of the vesicle is unclear. Ca/P-stimulated macrophages externalized PS, suggesting that nucleation may take place on the outer Mac-MV membrane (FIG. 3G).

S100A9 as a Mediator of Mineralization.

Figure 4:
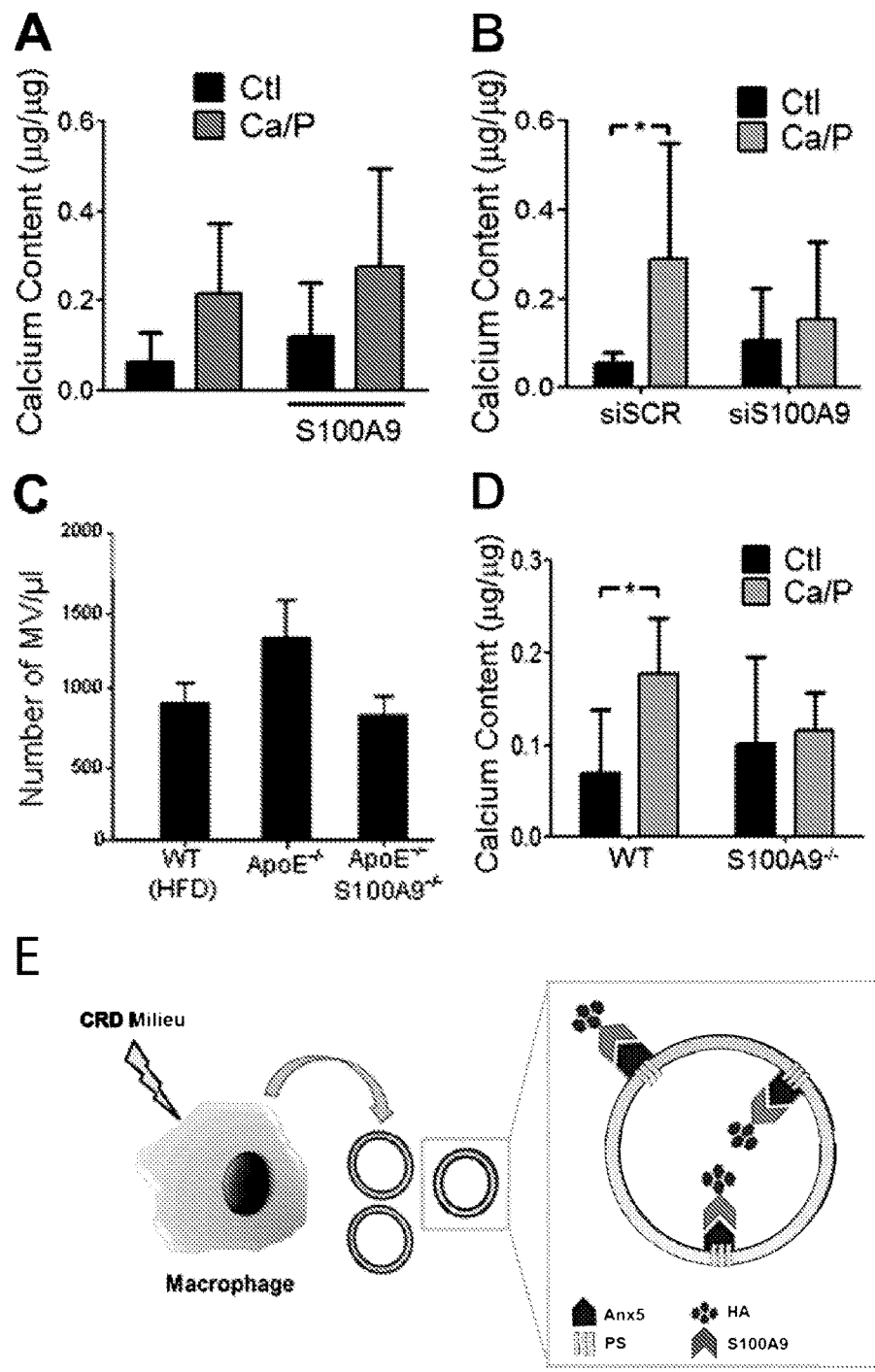
FIGS. 4A-4E show that S100A9 participates in MV calcification.

To address the mechanisms for the mineralization of Mac-MV, we examined the contribution of S100A9 in gain-of-function and loss-of-function studies. The addition of S100A9 in vitro tended to enhance the calcific potential of Mac-MV (FIG. 4A). S100A9 siRNA treatment in human macrophages (FIG. 9 for silencing efficacy) partially decreased the calcific potential of Mac-MV (FIG. 4B). To furnish further evidence in vivo for the function of S100A9 as a mediator of the calcific potential of Mac-MV, we performed loss-of-function experiments using S100A9$^{-/-}$ apoE$^{-/-}$ mice. More MV were quantified in mouse plasma of fat-fed apoE$^{-/-}$ mice than in fat-fed wild-type (WT) mice. Inactivation of the S100A9 gene in apoE$^{-/-}$ mice decreased MV in plasma to the levels of WT mice (FIG. 4C). In addition, Ca/P-stimulated S100A9$^{-/-}$ mouse peritoneal macrophages released Mac-MV with a lower calcific potential than those isolated from WT mice (FIG. 4D).

The work presented herein discloses a novel pathway of microcalcification that involves macrophage-derived MV. Concentrations of extracellular Ca and P, similar to those found in serum of CRD patients on dialysis, induced the release of Mac-MV with higher calcification potential. These findings support the operation of a new additional mechanism of arterial calcification that likely accelerates the excessive intimal and medial calcification associated with CRD. Without wishing to be bound by a theory, due to the relative abundance of macrophages over SMC in rupture-prone plaques (Libby P. & Aikawa M., Nat Med., 2002, 8:1257-62), macrophage-derived MV play a substantial role in the generation of microcalcification.

Mac-MV shared similarities with previously reported chondrocyte-derived MV (e.g. PS and Anx5 expression, Kirsch et al., *J Bone Miner Res.,* 2003, 18:1872-81) and exosomes (CD9 and TSG101). Mineralization of growth plate chondrocytes by MV requires PS, and Anx5; indeed other annexins may compensate for loss of Anx5 (Grskovic et al., J Bone Miner Res., 2012, online first). This present study found increased S100A9 and Anx5 expression in calcifying mac-MV, highlighting their potential importance in MV calcification. The results provide evidence that supports the concept that S100A9 interacts with Anx5, forming a PS-Anx5-S100A9 membrane complex, which acts as a nucleation site for hydroxyapatite (FIG. 4E).

The use of compound mutant mice in addition to gain-of-function and loss-of-function in vitro experiments, permitted dissection of the S100A9-dependent mechanism for formation of calcifying macrophage-derived MV in vivo. Previous studies identified S100A9-positive macrophages in early atherosclerotic lesions and suggested the role of this calcium-binding protein in vascular inflammation (Croce et al., *Circulation,* 2009, 120:427-36). The present evidence implicates S100A9 in the mineralization of macrophage-derived MV.

This study provides new insight into the pathogenesis of arterial calcification, particularly microcalcification—a contributor to the acute thrombotic complications of atherosclerosis. Despite its clinical challenge, we currently lack treatments and diagnostic tools to prevent or reverse cardiovascular calcification. Molecular imaging provided a novel technique for visualizing calcifying vesicular structures, which could potentially be translated to the clinic. The evidence provided should help to develop therapies for this unmet medical need including valvular as well as arterial calcification. Specifically, modulation of expression or function of S100A9 and/or Anx5 may suppress nucleation of hydroxyapatite by macrophage-derived MV and generation of microcalcification in "spotty" plaques prone to rupture, thus preventing the onset of devastating clinical complications.

The data presented herein show that macrophages associated with regions of calcified vesicular structures in human carotid plaques (n=136 patients). In vitro, macrophages released MV with high calcification and aggregation potential. MV expressed exosomal markers (CD9 and TSG101), and contain S100A9 and annexin V (Anx5). Silencing S100A9 in vitro and genetic deficiency in S100A9$^{-/-}$ mice reduced MV calcification, while stimulation with S100A9 increased calcification potential. Externalization of phosphatidylserine (PS) after Ca/P stimulation and interaction of S100A9 and Anx5, indicated that a PS-Anx5-S100A9 membrane complex facilitates hydroxyapatite nucleation within the macrophage-derived MV membrane. Thus, the results presented herein demonstrate the novel concept that macrophages release calcifying MV, enriched in S100A9 and Anx5, which contribute to accelerated microcalcification formation in CRD.

In the work presented in this study, the inventors have shown that macrophages contribute to arterial and aortic valve calcification by releasing matrix vesicles, precursors of microcalcifications. Calcifying matrix vesicles bud from the membrane of the living cells, aggregate and form large calcification regions. This unexpected and novel mechanism is an alternative pathway to a commonly accepted mechanisms of osteogenic transition or apoptotic cell death. Once stimulated by pro-inflammatory or pro-atherogenic cues, a complex forms in the membrane, which enables the matrix vesicles to increase in calcium content and thus calcify. The data presented in this shows that this complex is formed of phosphatidylserine, annexin V/VI and S100A9/S100A12. Thus, preventing this complex to form by targeting/blocking one of these components can block the calcification of the matrix vesicles and thereby prevent the nucleation of hydroxyapatite. In addition, the suppression/modulation of the release of matrix vesicles from macrophages can also attenuate cardiovascular calcification (e.g., coronary and aortic valve calcification) and other diseases associated with imbalance of osteoblastic/osteoclastic activity (e.g., osteoporosis). For proof of mechanism studies, lead indications can include calcification after transcatheter aortic valve implantation, and rapidly developing arterial and aortic valve calcification in patients with mineral imbalance and calcium/phosphate disorders, including chronic renal disease, hemodyalysis and diabetes. In addition, indications include arterio-venous grafts/shunts and vascular grafts (e.g., vein grafts for peripheral arterial disease or occlusive coronary arteries) in these patients at risk that are often occluded within a year. In the near future, tissue engineered vascular and valvular implants in such patients will be target indications. In addition, patients with Paget's disease, diabetes, rheumatoid arthritis, osteoporosis or osteoarthritis can be targets. The majority of these disorders have high rates of acute changes, making clinical development easier than chronic atherosclerosis.

In this study, the inventors used various stimuli to increase the calcific potential of macrophage-derived matrix vesicles, including stimuli associated with atherosclerotic calcification, and atherosclerotic calcification associated with chronic renal disease (CRD) and diabetes. The concentrations of calcium and phosphate used to stimulate the production of calcifying matrix vesicles by the inventors were comparable to those observed in patients with CRD. Cardiovascular calcification associated with disorders, such as CRD and diabetes, is thought to be multifactorial. It occurs in response to altered calcium and phosphate metabolism and has been demonstrated to be the result of an imbalance of inhibitors and inducers of mineralization (Shanahan C M et al 2007). The intima and media of the arteries have been observed to calcify in patients with these disorders. Medial calcification has been noted to occur without the infiltration of macrophages (Bostrom K. et al 2005). However, preclinical and clinical evidence suggests that CRD promotes pro-inflammatory milieu and accelerates the development of atherosclerosis and intimal calcification (Gross M L, Clin J Am Soc Nephrol, 2007, or, Nakamura S, Clin J Am Soc Nephrol. 2009). Calcification associated with diabetes and CRD has been suggested to be initiated via matrix vesicle-nucleated mineralization (Tanimura A 1986; Shao J S, Towler, 2006; Aikawa E et al, Circulation 2007).

The surprising and unexpected finding by the inventors that macrophages release calcifying matrix vesicles provides new foci for hydroxyapatite nucleation resulting in the generation of microcalcifications. The generation of microcalcifications is already known to occur in the presence of inflammation and lesions in the early stages of calcification; plaques such as these are often described as "spotty" calcifications (Aikawa E et al 2007). These 'spotty' calcifications located in the thin (<65 µm) fibrous cap overlying the necrotic core of atherosclerotic plaques are seen as dangerous, as they are more likely to cause plaque rupture due to debonding (Virmani R 2006) and lead to acute thrombosis and even sudden death due to fatal myocardial infarction (Huang H 2001; Vengrenyuk et al 2006; Vengrenyuk et al 2008; Hoshino T et al 2009). Therefore halting the production of these microcalcifications can prevent the progression of intimal atherosclerotic calcification at the early stages of this disease. Thus, molecules that suppress/modulate the release of matrix vesicles from macrophages can attenuate cardiovascular calcification (e.g., coronary and aortic valve calcification) and other diseases associated with imbalance of osteoblastic/osteoclastic activity (e.g., osteoporosis).

To inventors' knowledge, this is the first report to demonstrate a direct role of macrophages in inflammation-driven calcification. It is an unexpected and surprising finding that macrophages produce matrix vesicles, similar in size and structure (as seen using electron microscopy), to those previously visualized in atherosclerotic plaques (Bobryshev et al. 2006; Kasputin et al. 2011), and that that they have the potential to calcify and thus act as nucleation sites in cardiovascular disease.

Effectiveness of the method described herein can be determined using indications such as relatively acute calcific changes after transcatheter aortic valve implantation; rapidly developing arterial and aortic valve calcification in patients with mineral imbalance and calcium/phosphate disorders, including chronic renal disease, hemodyalysis and diabetes; arterio-venous shunts; arterial and vein grafts; and tissue engineered vascular and valvular implants, Paget's disease, rheumatoid arthritis, osteoporosis or osteoarthritis. The majority of these disorders have high rates of acute changes (e.g., months rather than years).

REFERENCES

1. Libby P, Aikawa M. Stabilization of atherosclerotic plaques: new mechanisms and clinical targets. *Nat Med.* 2002; 8:1257-62.
2. Li R, Mittelstein D, Lee J, Fang K, Majumdar R, Tintut Y, Demer L L, Hsiai T K. A dynamic model of calcific nodule destabilization in response to monocyte- and oxidized lipid-induced matrix metalloproteinases. *Am J Physiol Cell Physiol.* 2012; 302:C658-C665.
3. Wenk J F, Papadopoulos P, Zohdi T I. Numerical modeling of stress in stenotic arteries with microcalcifications: a micromechanical approximation. *J Biomech Eng.* 2010; 132:091011.
4. Aikawa E, Aikawa M, Libby P, Figueiredo J L, Rusanescu G, Iwamoto Y, Fukuda D, Kohler R H, Shi G P, Jaffer F A, Weissleder R. Arterial and aortic valve calcification abolished by elastolytic cathepsin S deficiency in chronic renal disease. *Circulation.* 2009; 119:1785-94.
5. Goodman W G, London G, Amann K, Block G A, Giachelli C, Hruska K A, Ketteler M, Levin A, Massy Z, McCarron D A, Raggi P, Shanahan C M, Yorioka N. Vascular calcification in chronic kidney disease. *Am J Kidney Dis.* 2004; 43:572-9.
6. Chen N X, O'Neill K D, Chen X, Moe S M. Annexin-mediated matrix vesicle calcification in vascular smooth muscle cells. *J Bone Miner Res.* 2008; 23:1798-805.
7. Kapustin A N, Davies J D, Reynolds J L, McNair R, Jones G T, Sidibe A, Schurgers L J, Skepper J N, Proudfoot D, Mayr M, Shanahan C M. Calcium regulates key components of vascular smooth muscle cell-derived matrix vesicles to enhance mineralization. *Circ Res.* 2011; 109: e1-12.
8. Anderson H C. Matrix vesicles and calcification. *Curr Rheumatol Rep.* 2003; 5:222-6.
9. Kim K M. Calcification of matrix vesicles in human aortic valve and aortic media. *Fed Proc.* 1976; 35:156-62.
10. Aikawa E, Nahrendorf M, Figueiredo J L, Swirski F K, Shtatland T, Kohler R H, Jaffer F A, Aikawa M, Weissleder R. Osteogenesis associates with inflammation in early-stage atherosclerosis evaluated by molecular imaging in vivo. *Circulation.* 2007; 116:2841-50.
11. New S E, Aikawa E. Molecular imaging insights into early inflammatory stages of arterial and aortic valve calcification. *Circ Res.* 2011; 108:1381-91.
12. Kirsch T, Wang W, Pfander D. Functional differences between growth plate apoptotic bodies and matrix vesicles. *J Bone Miner Res.* 2003; 18:1872-81.
13. McCormick M M, Rahimi F, Bobryshev Y V, Gaus K, Zreiqat H, Cai H, Lord R S, Geczy C L. S100A8 and S100A9 in human arterial wall. Implications for atherogenesis. *J Biol Chem.* 2005; 280:41521-9.
14. Bode G, Luken A, Kerkhoff C, Roth J, Ludwig S, Nacken W. Interaction between S100A8/A9 and annexin A6 is involved in the calcium-induced cell surface exposition of S100A8/A9. *J Biol Chem.* 2008; 283:31776-84.
15. Grskovic I, Kutsch A, Frie C, Groma G, Stermann J, Schlötzer-Schrehardt U, Nieholf, A, Moss, S E, Rosenbaum, S, Pöschl E, Chmielewski, M, Rappl, G, Abken, H, Bateman, J F, Cheah, K S, Paulsson, M, Brachvogel, B. Depletion of annexin A S, annexin A6 and collagen X causes no gross changes in matrix vesicle mediated mineralization, but lack of collagen X affects hematopoiesis and the Th1/Th2 response. J Bone Miner Res. 2012:online first.
16. Croce K, Gao H, Wang Y, Mooroka T, Sakuma M, Shi C, Sukhova G K, Packard R R, Hogg N, Libby P, Simon D I. Myeloid-related protein-8/14 is critical for the biological response to vascular injury. *Circulation.* 2009; 120:427-36.
17. Aikawa, E., Nahrendorf, M., Figueiredo, J. L., Swirski, F. K., Shtatland, T., Kohler, R. H., Jaffer, F. A., Aikawa, M., & Weissleder, R. Osteogenesis associates with inflammation in early-stage atherosclerosis evaluated by molecular imaging in vivo. *Circulation.* 2007; 116:2841-2850
18. Aikawa, E., Nahrendorf, M., Sosnovik, D., Lok, V. M., Jaffer, F. A., Aikawa, M., & Weissleder, R. Multimodality molecular imaging identifies proteolytic and osteogenic activities in early aortic valve disease. *Circulation.* 2007; 115:377-386

19. Aikawa, M., Rabkin, E., Sugiyama, S., Voglic, S. J., Fukumoto, Y., Furukawa, Y., Shiomi, M., Schoen, F. J., & Libby, P. An HMG-CoA reductase inhibitor, cerivastatin, suppresses growth of macrophages expressing matrix metalloproteinases and tissue factor in vivo and in vitro. *Circulation*. 2001; 103:276-283
20. Tzur, A., Moore, J. K., Jorgensen, P., Shapiro, H. M., Kirschner, M. W. Optimizing optical flow cytometry for cell volume-based sorting and analysis. *PLoS One*. 2011; 6:e16053
21. Neto. J. C., Agero, U., Gazzinelli, R. T., Mesquita, O. N. Measuring optical and mechanical properties of a living cell with defocusing microscopy. Biophys J. 2006; 91:1108-1115

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A method for inhibiting calcification of a macrophage derived matrix vesicle (MV), the method comprising contacting a macrophage with a compound, wherein the compound inhibits expression level of a nucleic acid encoding S100A9 in the macrophage, wherein the compound is a nucleic acid and directly inhibits the expression level of the nucleic acid encoding S100A9.

2. The method of claim 1, wherein the compound is an siRNA.

3. The method of claim 1, wherein the compound inhibits the expression of the nucleic acid encoding S100A9 in the macrophage by at least 10% relative to a control or reference level, and wherein the control or reference level is a level in absence of the compound.

4. The method of claim 1, wherein the nucleic acid encoding S100A9 is an mRNA.

5. The method of claim 1, wherein said contacting is in a subject in need of inhibition of calcification, wherein the calcification is arterial or aortic valve calcification.

6. A method for inhibiting calcification in a subject, the method comprising administering a therapeutically effective amount of a compound to a subject in need thereof, wherein the compound inhibits expression level of a nucleic acid encoding S100A9 in the macrophage SMC, or interstitial valvular cell, and wherein the compound is a nucleic acid and directly inhibits the expression level of the nucleic acid encoding S100A9, wherein the calcification is arterial or aortic valve calcification.

7. The method of claim 6, wherein the compound is an siRNA.

8. The method of claim 6, wherein the compound inhibits the expression of the nucleic acid encoding S100A9 in the macrophage by at least 10% relative to a control or reference level, and wherein the control or reference level is a level in absence of the compound.

9. The method of claim 6, wherein the nucleic acid encoding S100A9 is mRNA.

10. The method of claim 6, wherein said administering is implant, injection, infusion, instillation, implantation, or ingestion.

11. The method of claim 6, wherein the therapeutically effective amount is from about 1 µg/kg to about 150 mg/kg of body weight.

12. The method of claim 6, wherein said administering is once a day.

* * * * *